United States Patent
Rourke et al.

(10) Patent No.: US 7,179,291 B2
(45) Date of Patent: Feb. 20, 2007

(54) METHOD AND APPARATUS FOR IMPROVING MITRAL VALVE FUNCTION

(75) Inventors: Johnathan M. Rourke, Belmont, MA (US); Daniel C. Taylor, Brighton, MA (US); Steven J. Blacker, Brookline, MA (US); Terrence G. Barnes, Somerville, MA (US)

(73) Assignee: Viacor, Inc., Wilmington, MA (US)

( * ) Notice: Subject to any disclaimer, the term of this patent is extended or adjusted under 35 U.S.C. 154(b) by 0 days.

(21) Appl. No.: 10/894,676

(22) Filed: Jul. 19, 2004

(65) Prior Publication Data

US 2005/0070998 A1 Mar. 31, 2005

Related U.S. Application Data

(63) Continuation-in-part of application No. 10/446,470, filed on May 27, 2003.

(60) Provisional application No. 60/562,958, filed on Apr. 17, 2004, provisional application No. 60/489,549, filed on Jul. 23, 2003.

(51) Int. Cl.
*A61F 2/24* (2006.01)

(52) U.S. Cl. ................. 623/2.36; 604/525

(58) Field of Classification Search ........... 623/2.37, 623/2.36; 600/585; 604/524, 525
See application file for complete search history.

(56) References Cited

U.S. PATENT DOCUMENTS

| | | | |
|---|---|---|---|
| 4,266,999 A * | 5/1981 | Baier | ............... 604/175 |
| 4,535,757 A | 8/1985 | Webster | |
| 4,669,473 A | 6/1987 | Richards et al. | |
| 4,917,698 A | 4/1990 | Carpentier et al. | |
| 4,944,745 A | 7/1990 | Sogard et al. | |
| 5,061,277 A | 10/1991 | Carpentier et al. | |
| 5,092,889 A | 3/1992 | Campbell, Jr. | |
| 5,133,732 A | 7/1992 | Wiktor | |
| 5,195,972 A | 3/1993 | Inoue | |
| 5,269,809 A | 12/1993 | Hayhurst et al. | |
| 5,332,402 A | 7/1994 | Teitelbaum | |
| 5,345,937 A * | 9/1994 | Middleman et al. | ........ 604/523 |
| 5,383,892 A | 1/1995 | Cardon et al. | |
| 5,389,091 A | 2/1995 | Moorehead | |

(Continued)

FOREIGN PATENT DOCUMENTS

DE 101 61 543.4 12/2002

(Continued)

OTHER PUBLICATIONS

Buchanan, Circumferential Suture of the Mitral Annulus for Correction of Mitral Regurgitation in Dogs, Veterinary Surgery, 1998, 182-193, vol. 27.

(Continued)

*Primary Examiner*—Brian E. Pellegrino
(74) *Attorney, Agent, or Firm*—Pandiscio & Pandiscio

(57) ABSTRACT

A method and apparatus for reducing mitral regurgitation. The apparatus is inserted into the coronary sinus of a patient in the vicinity of the posterior leaflet of the mitral valve, the apparatus being adapted to straighten the natural curvature of at least a portion of the coronary sinus in the vicinity of the posterior leaflet of the mitral valve, whereby to move the posterior annulus anteriorly and thereby improve leaflet coaptation and reduce mitral regurgitation.

29 Claims, 25 Drawing Sheets

U.S. PATENT DOCUMENTS

| | | |
|---|---|---|
| 5,443,481 A | 8/1995 | Lee |
| 5,462,530 A | 10/1995 | Jang |
| 5,476,506 A | 12/1995 | Lunn |
| 5,509,900 A | 4/1996 | Kirkman |
| 5,514,092 A | 5/1996 | Forman et al. |
| 5,545,209 A | 8/1996 | Roberts et al. |
| 5,562,620 A | 10/1996 | Klein et al. |
| 5,569,201 A | 10/1996 | Burns |
| 5,575,799 A | 11/1996 | Bolanos et al. |
| 5,681,345 A | 10/1997 | Euteneuer |
| 5,720,726 A | 2/1998 | Marcadis et al. |
| 5,743,875 A | 4/1998 | Sirhan et al. |
| 5,755,778 A | 5/1998 | Kleshinski |
| 5,755,781 A | 5/1998 | Jayaraman |
| 5,800,495 A | 9/1998 | Machek et al. |
| 5,800,526 A | 9/1998 | Anderson et al. |
| 5,855,565 A | 1/1999 | Bar-Cohen et al. |
| 5,911,732 A | 6/1999 | Hojeibane |
| 5,911,752 A | 6/1999 | Dustrude et al. |
| 5,957,949 A | 9/1999 | Leonhardt et al. |
| 5,968,009 A * | 10/1999 | Siman .................. 604/523 |
| 5,980,570 A | 11/1999 | Simpson |
| 5,984,917 A | 11/1999 | Fleischman et al. |
| 6,033,436 A | 3/2000 | Steinke et al. |
| 6,051,020 A | 4/2000 | Goicoechea et al. |
| 6,090,136 A | 4/2000 | McDonald et al. |
| 6,071,263 A | 6/2000 | Kirkman |
| 6,086,599 A | 7/2000 | Lee et al. |
| 6,102,945 A | 8/2000 | Campbell |
| 6,119,037 A | 9/2000 | Kellogg et al. |
| 6,162,245 A | 12/2000 | Jayaraman |
| 6,165,194 A | 12/2000 | Denardo |
| 6,187,040 B1 | 2/2001 | Wright |
| 6,210,432 B1 | 4/2001 | Solem et al. |
| 6,241,746 B1 | 6/2001 | Bosma et al. |
| 6,258,117 B1 | 7/2001 | Camrud et al. |
| 6,277,107 B1 | 8/2001 | Lurie et al. |
| 6,287,336 B1 | 9/2001 | Globerman et al. |
| 6,328,765 B1 | 12/2001 | Hardwick et al. |
| 6,332,896 B1 | 12/2001 | Hubbard et al. |
| 6,402,781 B1 | 6/2002 | Langberg et al. |
| 6,419,696 B1 | 7/2002 | Ortiz et al. |
| 6,524,301 B1 * | 2/2003 | Wilson et al. ........... 604/523 |
| 6,537,314 B2 | 3/2003 | Langberg et al. |
| 6,569,198 B1 | 5/2003 | Wilson et al. |
| 6,585,716 B2 | 7/2003 | Altman |
| 6,602,288 B1 | 8/2003 | Cosgrove et al. |
| 6,638,268 B2 | 10/2003 | Niazi |
| 6,648,874 B2 | 11/2003 | Parisi et al. |
| 6,656,221 B2 | 12/2003 | Taylor et al. |
| 6,676,702 B2 | 1/2004 | Mathis |
| 6,706,065 B2 | 3/2004 | Langberg et al. |
| 6,709,456 B2 | 3/2004 | Langberg et al. |
| 6,800,090 B2 | 10/2004 | Alferness et al. |
| 6,805,710 B2 | 10/2004 | Bolling et al. |
| 6,810,882 B2 | 11/2004 | Langberg et al. |
| 6,827,731 B2 | 12/2004 | Armstrong et al. |
| 6,908,478 B2 | 6/2005 | Alferness et al. |
| 6,949,122 B2 | 9/2005 | Adams et al. |
| 2001/0018611 A1 | 8/2001 | Solem et al. |
| 2002/0087173 A1 | 7/2002 | Alferness et al. |
| 2002/0151961 A1 | 10/2002 | Lashinski et al. |
| 2002/0183838 A1 | 12/2002 | Liddicoat et al. |
| 2003/0069636 A1 | 4/2003 | Solem et al. |
| 2003/0078654 A1 | 4/2003 | Taylor et al. |
| 2003/0130730 A1 | 7/2003 | Cohn et al. |
| 2004/0019377 A1 | 1/2004 | Taylor et al. |
| 2005/0222678 A1 | 10/2005 | Lashinski et al. |

FOREIGN PATENT DOCUMENTS

| | | |
|---|---|---|
| EP | 0756853 A1 | 2/1997 |
| JP | 409322936 A | 12/1997 |
| WO | WO 98/22159 A2 | 5/1998 |
| WO | WO 00/62708 | 10/2000 |
| WO | WO 01/00111 A1 | 1/2001 |
| WO | WO 01/54618 A1 | 8/2001 |
| WO | WO 02/053206 A2 | 7/2002 |
| WO | WO 02/060352 A1 | 8/2002 |
| WO | WO 02/062263 A2 | 8/2002 |
| WO | WO 02/062270 A1 | 8/2002 |
| WO | WO 02/091908 A2 | 11/2002 |
| WO | WO 02/100240 A2 | 12/2002 |
| WO | WO 03/037171 A2 | 5/2003 |

OTHER PUBLICATIONS

Kerstetter, et al., Short-Term Hemodynamic Evaluation of Circumferential Mitral Annuloplasty for Correction of Mitral Valve Regurgitation in Dogs, Veterniary Surgery, 1998, 216-223, vol. 27.

Beardow, et al., Chronic Mitral Valve Disease in Cavalier King Charles Spaniels: 95 cases (1987-1991), Journal of the American Veterinary Medicial Association, Oct. 1, 1993, 1023-1029, vol. 203, No. 7.

Davila, et al., Circumferential Suture of the Mitral Ring: A Method for the Surgical Correction of Mitral Insufficiency, 1955, 531-563, C.V. Moshy Company, St. Louis.

Glover, et al., The Treatment of Mitral Valve Insufficiency by the Purse-String Technique, The Journal of Thoracic Surgery, Jan. 1957, 75-101, vol. 33.

Davila, et al., Circumferential Suture of the Mitral Valve for the Correction of Regurgitation, The American Journal of Cardiology, Inc., Sep. 1958, 267-275.

Buchanan, Causes and Prevalence of Cardiovascular Disease, Current Veterinary Therapy XI, 1992, 647-655, WB Saunders Co.

* cited by examiner

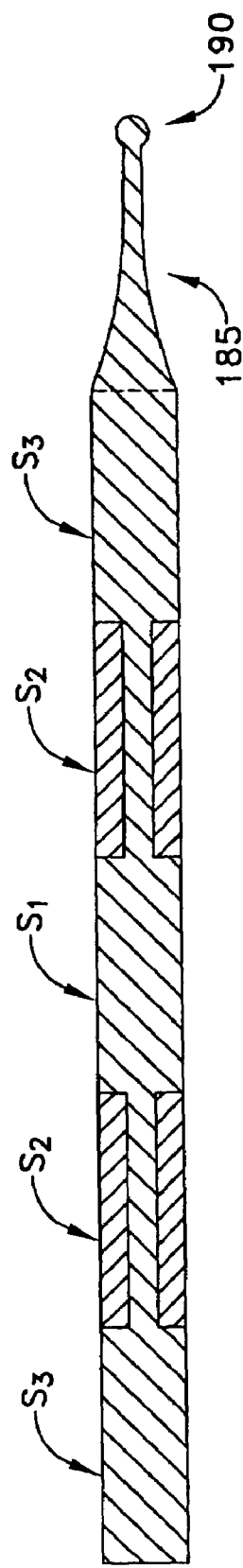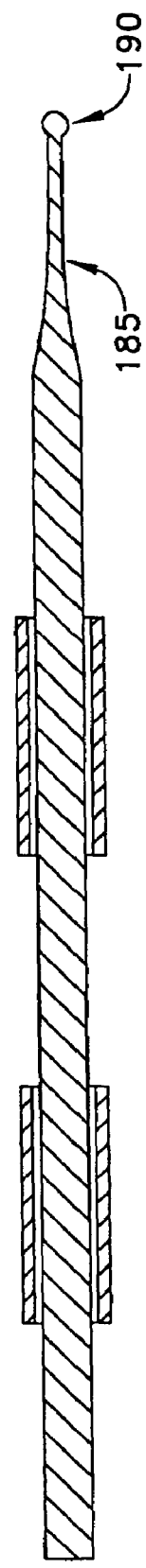

| Stiffness | Straightening Rods (L= $S_3 + S_2$) | | |
|---|---|---|---|
| | L=25 mm | L=35 mm | L=45 mm |
| 200 grams cm | D type | E type | F type |
| 100 grams cm | A type | B type | C type |
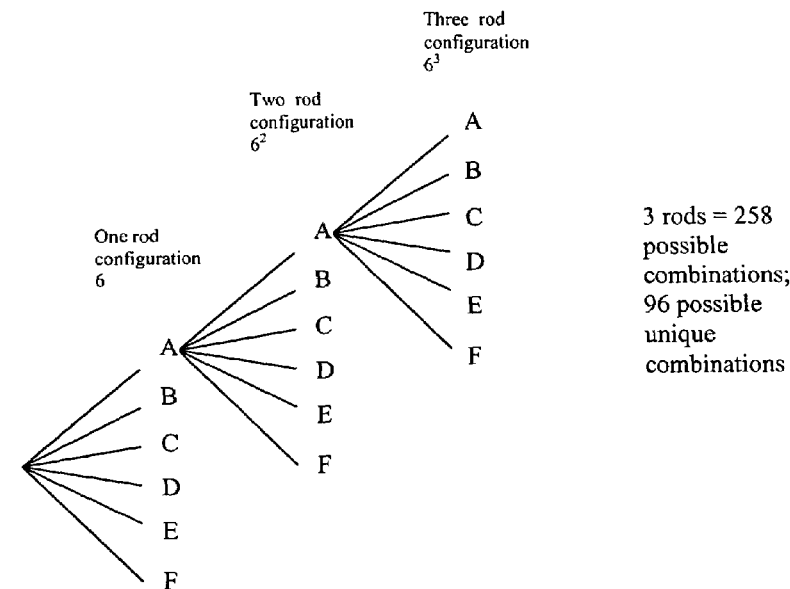
3 rods = 258 possible combinations; 96 possible unique combinations
| System Stiffness | Possible Straightening Rod Combinations | | |
|---|---|---|---|
| | 25 mm | 35 mm | 45 mm |
| 600 | 3x200 | 3x200 | 3x200 |
| 500 | 2x200,1x100 | 2x200,1x100 | 2x200,1x100 |
| 400 | 2x200<br>1x200, 2x100 | 2x200<br>1x200, 2x100 | 2x200<br>1x200, 2x100 |
| 300 | 1x200,1x100<br>3x100 | 1x200,1x100<br>3x100 | 1x200,1x100<br>3x100 |
| 200 | 1x200<br>2x100 | 1x200<br>2x100 | 1x200<br>2x100 |
| 100 | 1x100 | 1x100 | 1x100 |
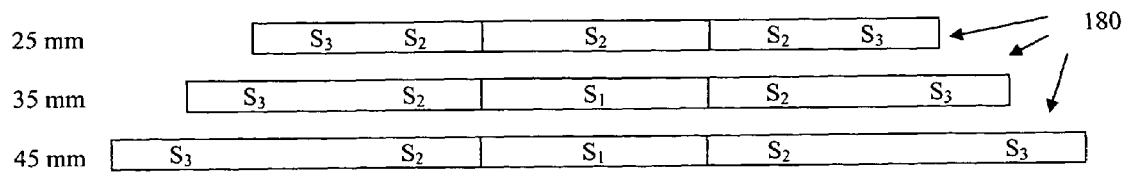
$L = S_3 + S_2$
FIG. 14A

METHOD AND APPARATUS FOR IMPROVING MITRAL VALVE FUNCTION

REFERENCE TO PENDING PRIOR PATENT APPLICATIONS

This patent application is a continuation-in-part of pending prior U.S. patent application Ser. No. 10/446,470, filed May 27, 2003 by Jonathan Rourke et al. for METHOD AND APPARATUS FOR IMPROVING MITRAL VALVE FUNCTION.

This patent application also claims benefit of (1) prior U.S. Provisional Patent Application Ser. No. 60/489,549, filed Jul. 23, 2003, now abandoned, by Jonathan M. Rourke for METHOD AND APPARATUS FOR IMPROVING MITRAL VALVE FUNCTION, and (2) prior U.S. Provisional Patent Application Ser. No. 60/562,958, filed Apr. 17, 2004, now abandoned by Jonathan M. Rourke for METHOD AND APPARATUS FOR IMPROVING MITRAL VALVE FUNCTION.

The three above-identified patent applications are hereby incorporated herein by reference.

FIELD OF THE INVENTION

This invention relates to surgical methods and apparatus in general, and more particularly to surgical methods and apparatus for improving mitral valve function.

BACKGROUND OF THE INVENTION

The mitral valve is located in the heart between the left atrium and the left ventricle. A properly functioning mitral valve permits blood to flow from the left atrium to the left ventricle when the left ventricle expands (i.e., during diastole), and prevents the regurgitation of blood from the left ventricle back into the left atrium when the left ventricle contracts, i.e., during systole.

In some circumstances the mitral valve may fail to function properly, such that regurgitation may occur. By way of example, mitral regurgitation is a common occurrence in patients with heart failure. Mitral regurgitation in patients with heart failure is caused by changes in the geometric configurations of the left ventricle, papillary muscles and mitral annulus. These geometric alterations result in incomplete coaptation of the mitral leaflets at systole. In this situation, mitral regurgitation is generally corrected by plicating the mitral valve annulus so as to reduce the circumference of the distended annulus and restore the original geometry of the mitral valve annulus.

More particularly, current surgical practice for mitral valve repair generally requires that the mitral valve annulus be reduced in radius by surgically opening the left atrium and then fixing sutures, or more commonly sutures in combination with a support ring, to the internal surface of the annulus; this structure is used to cinch the annulus, in a pursestring-like fashion, to a smaller radius, thereby improving leaflet coaptation and reducing mitral regurgitation.

This method of mitral valve repair, generally termed "annuloplasty", effectively reduces mitral regurgitation in heart failure patients. This, in turn, reduces symptoms of heart failure, improves quality of life and increases longetivity. Unfortunately, however, the invasive nature of such mitral valve surgery (i.e., general anesthesia, chest wall incision, cardiopulmonary bypass, cardiac and pulmonary arrest, and an incision on the heart itself so as to gain access to the mitral valve), and the risks associated therewith, render most heart failure patients poor surgical candidates. Thus, a less invasive means to increase leaflet coaptation and thereby reduce mitral regurgitation in heart failure patients would make this therapy available to a much greater percentage of patients.

Mitral regurgitation also occurs in approximately 20% of patients suffering acute myocardial infarction. In addition, mitral regurgitation is the primary cause of cardiogenic shock in approximately 10% of patients who develop severe hemodynamic instability in the setting of acute myocardial infarction. Patients with mitral regurgitation and cardiogenic shock have about a 50% hospital mortality. Elimination of mitral regurgitation in these patients would be of significant benefit. Unfortunately, however, patients with acute mitral regurgitation complicating acute myocardial infarction are particularly high-risk surgical candidates, and are therefore not good candidates for a traditional annuloplasty procedure. Thus, a minimally invasive means to effect a temporary reduction or elimination of mitral regurgitation in these critically ill patients would afford them the time to recover from the myocardial infarction or other acute life-threatening events and make them better candidates for other medical, interventional or surgical therapy.

SUMMARY OF THE INVENTION

As a result, one object of the present invention is to provide an improved method for reducing mitral regurgitation.

Another object of the present invention is to provide an improved apparatus for reducing mitral regurgitation.

These and other objects are addressed by the present invention, which comprises an improved method and apparatus for reducing mitral regurgitation.

In one form of the invention, there is provided a method for reducing mitral regurgitation comprising:

inserting apparatus into the coronary sinus of a patient in the vicinity of the posterior leaflet of the mitral valve, the apparatus having a distal end, a proximal end and an intermediate portion, and the apparatus being configured so that when the apparatus is positioned in the coronary sinus in the vicinity of the posterior leaflet of the mitral valve, the distal and proximal ends will apply a posteriorly-directed force to the walls of the coronary sinus and the intermediate portion will apply an anteriorly-directed force to the walls of the coronary sinus, whereby to move the posterior annulus anteriorly and thereby improve leaflet coaptation and reduce mitral regurgitation.

In another form of the invention, there is provided an apparatus for reducing mitral regurgitation comprising:

a body having a distal end, a proximal end and an intermediate portion, the body being configured so that when the body is positioned in the coronary sinus in the vicinity of the posterior leaflet of the mitral valve, the distal and proximal ends will apply a posteriorly-directed force to the walls of the coronary sinus, and the intermediate portion will apply an anteriorly-directed force to the walls of the coronary sinus, whereby to move the posterior annulus of the mitral valve anteriorly and thereby improve leaflet coaptation and reduce mitral regurgitation.

In another form of the invention, there is provided an assembly for reducing mitral regurgitation, the assembly comprising:

an elongated carrier of material sufficiently flexible to assume a first configuration generally conforming to a coronary sinus upon insertion of said carrier into the coronary sinus, and to assume a straighter second configuration when biased toward the straighter configuration, said carrier having a lumen extending lengthwise therethrough; and an elongated rod of a material less flexible than said carrier and adapted to be received by the lumen in said carrier;

whereby to urge said carrier from the first configuration to the second configuration, to straighten a natural curvature of at least a portion of the coronary sinus in the vicinity of the posterior leaflet of the mitral valve, to move the posterior annulus anteriorly and thereby improve leaflet coaptation and reduce mitral regurgitation.

In another form of the invention, there is provided an assembly for reducing mitral regurgitation, the assembly comprising:

an elongated carrier of material sufficiently flexible to assume a first configuration generally conforming to a coronary sinus upon insertion of said carrier into the coronary sinus, and to assume a straighter second configuration when biased toward the straighter configuration, said carrier having a plurality of lumens extending lengthwise therethrough; and a plurality of elongated rods of a material less flexible than said carrier and adapted to be received by the lumens in said carrier;

whereby to urge said carrier from the first configuration to the second configuration, to straighten a natural curvature of at least a portion of the coronary sinus in the vicinity of the posterior leaflet of the mitral valve, to move the posterior annulus anteriorly and thereby improve leaflet coaptation and reduce mitral regurgitation.

In another form of the invention, there is provided a method for reducing mitral regurgitation, the method comprising the steps of:

providing a flexible carrier having at least one lumen extending lengthwise therethrough;

advancing a guidewire through the vascular system of a patient until a distal end of the guidewire is disposed in the coronary sinus of the patient;

advancing the carrier over the guidewire until a distal end of the carrier is disposed in the coronary sinus;

advancing a rod of a selected stiffness into said at least one lumen to exert a straightening force on the carrier and thereby on the coronary sinus to move the annulus of the mitral valve anteriorly, whereby to reduce mitral regurgitation.

In another form of the invention, there is provided an assembly for reducing mitral regurgitation, the assembly comprising:

a carrier of material sufficiently flexible to assume a first configuration generally conforming to a coronary sinus upon insertion of said carrier into the coronary sinus, and to assume a straighter second configuration when biased toward the straighter configuration, said carrier having a plurality of first lumens extending lengthwise therethrough;

a catheter shaft having a plurality of first lumens extending lengthwise therethrough, each alignable with one of the carrier first lumens, a distal end of said catheter shaft being engageable with a proximal end of said carrier;

a plurality of straightening rods, each less flexible than said carrier and adapted to be received by the catheter shaft first lumens and by the carrier first lumens; and a push rod adapted to be received by at least the catheter shaft first lumens and engageable with one of said straightening rods and operable to push the one straightening rod into one of the carrier first lumens in alignment with the catheter shaft lumen in which said push rod is disposed;

whereby to bias the carrier from the first configuration to the second configuration.

In another form of the invention, there is provided an assembly for reducing mitral regurgitation, the assembly comprising:

an elongated carrier of material sufficiently flexible to assume a first configuration generally conforming to a coronary sinus upon insertion of said carrier into the coronary sinus, and to assume a straighter second configuration when biased toward the straighter configuration, said carrier having a plurality of first lumens extending lengthwise therethrough and a plurality of second lumens, smaller in diameter than the first lumens, extending therethrough;

a catheter shaft having a plurality of first and second lumens extending lengthwise therethrough and alignable with the respective first and second lumens of said carrier, a distal end of said catheter shaft being engageable with a proximal end of said carrier;

a plurality of straightening rods less flexible than said carrier and adapted to be received by the catheter shaft first lumens and by the carrier first lumens;

a plurality of push rods adapted to be received by at least the catheter shaft first lumens; and a tether fixed in at least one carrier second lumen and extending through the catheter shaft second lumen and manipulatable to draw said carrier into abutting engagement with said catheter shaft;

wherein at least one selected stiffening rod is insertable into at least one selected catheter shaft first lumen, and at least one push rod is insertable into the selected catheter shaft lumen and into engagement with the selected stiffening rod to push the selected stiffening rod into one of the carrier first lumens, to bias the carrier from the first configuration towards the second configuration.

In another form of the invention, there is provided a method for reducing mitral regurgitation, the method comprising the steps of:

inserting a guidewire into a patient's vascular system and into the coronary sinus;

loading a carrier onto the guidewire, the carrier being of a material sufficiently flexible to assume a first configuration generally conforming to the coronary sinus, the carrier having a plurality of first lumens extending lengthwise therethrough;

loading a catheter shaft onto the guidewire, the catheter shaft having a plurality of first lumens extending lengthwise therethrough and alignable with the carrier first lumens;

advancing the catheter shaft and the carrier distally along the guidewire until the carrier is disposed in the coronary sinus and adjacent the posterior leaflet of the mitral valve;

loading a straightening rod into a selected one of the catheter shaft first lumens, the straightening rod being of a material less flexible than the lumen;

loading a push rod into the catheter shaft selected first lumen;

engaging the straightening rod with the push rod and advancing the push rod distally to push the straightening rod distally into one of the carrier first lumens aligned with the selected catheter shaft first lumen to advance the engaged straightening rod into the carrier first lumen, to cause the carrier to assume a straighter second configuration;

whereby to apply an anteriorly-directed force to the posterior leaflet of the mitral valve, thereby to reduce mitral regurgitation.

In another form of the invention, there is provided a method for reducing mitral regurgitation, the method comprising the steps of:

providing a flexible carrier having at least one lumen extending lengthwise therethrough;

advancing a guidewire through the vascular system of a patient until a distal end of the guidewire is disposed in the coronary sinus of the patient;

advancing the carrier over the guidewire until a distal end of the carrier is disposed in the coronary sinus;

advancing a rod of a selected stiffness into said at least one lumen to exert a straightening force on the carrier and thereby on the coronary sinus to move the annulus of the mitral valve anteriorly, whereby to reduce mitral regurgitation;

positioning the proximal end of said flexible carrier in a tissue pocket.

In another form of the invention, there is provided a method for reducing mitral regurgitation, the method comprising the steps of:

providing a flexible carrier having at least one lumen extending lengthwise therethrough;

advancing a guidewire through the vascular system of a patient until a distal end of the guidewire is disposed in the coronary sinus of the patient;

advancing the carrier over the guidewire until a distal end of the carrier is disposed in the coronary sinus;

advancing a rod of a selected stiffness into said at least one lumen to exert a straightening force on the carrier and thereby on the coronary sinus to move the annulus of the mitral valve anteriorly, whereby to reduce mitral regurgitation;

cutting said flexible carrier to length;

positioning a bumper into at least one lumen;

capping the proximal end of said flexible carrier;

positioning the proximal end of said flexible carrier in a tissue pocket.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 7, 8, 9, 10 and 10A are schematic views showing different forms of straightening rods;

FIG. 14A is a schematic view illustrating how a kit of different straightening rods can provide a wide range of straightening forces;

DETAILED DESCRIPTION OF THE PREFERRED EMBODIMENTS

Overview

The coronary sinus is the largest vein in the human heart. During a large portion of its course in the atrioventricular groove, the coronary sinus typically extends adjacent to the left atrium of the heart for a distance of approximately 5 to 10 cm. Significantly, for a portion of its length, e.g., typically approximately 7–9 cm, the coronary sinus extends substantially adjacent to the posterior perimeter of the mitral annulus. The present invention takes advantage of this fact. More particularly, by deploying novel apparatus in the coronary sinus, adjacent to the posterior leaflet of the mitral valve, the natural curvature of the coronary sinus may be modified in the vicinity of the posterior leaflet of the mitral valve, whereby to move the posterior annulus anteriorly so as to improve leaflet coaptation and, as a result, reduce mitral regurgitation.

Patient Anatomy

Figure 1:
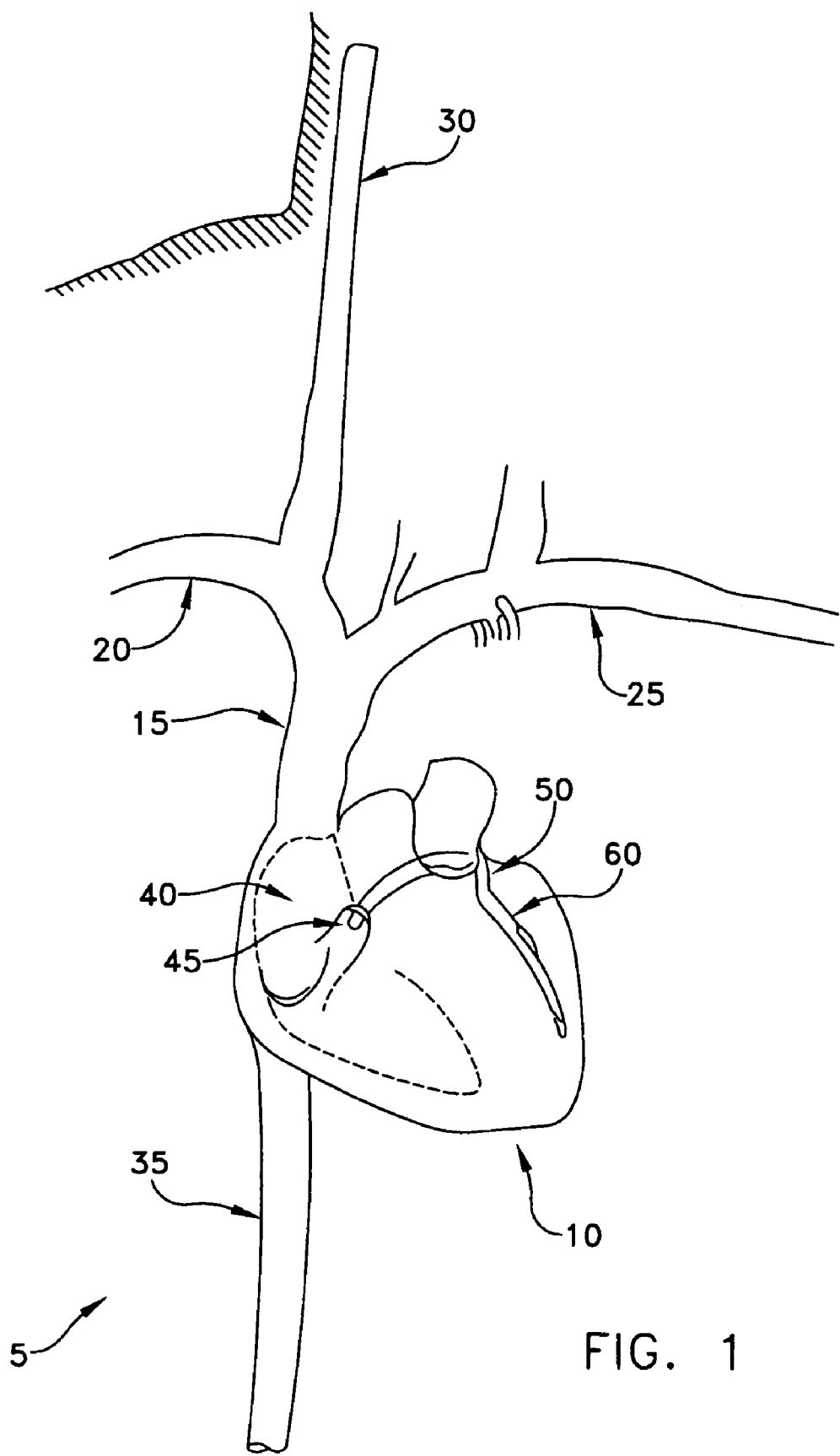
FIG. 1 is a schematic view of portions of the human vascular system.
Figure 2:
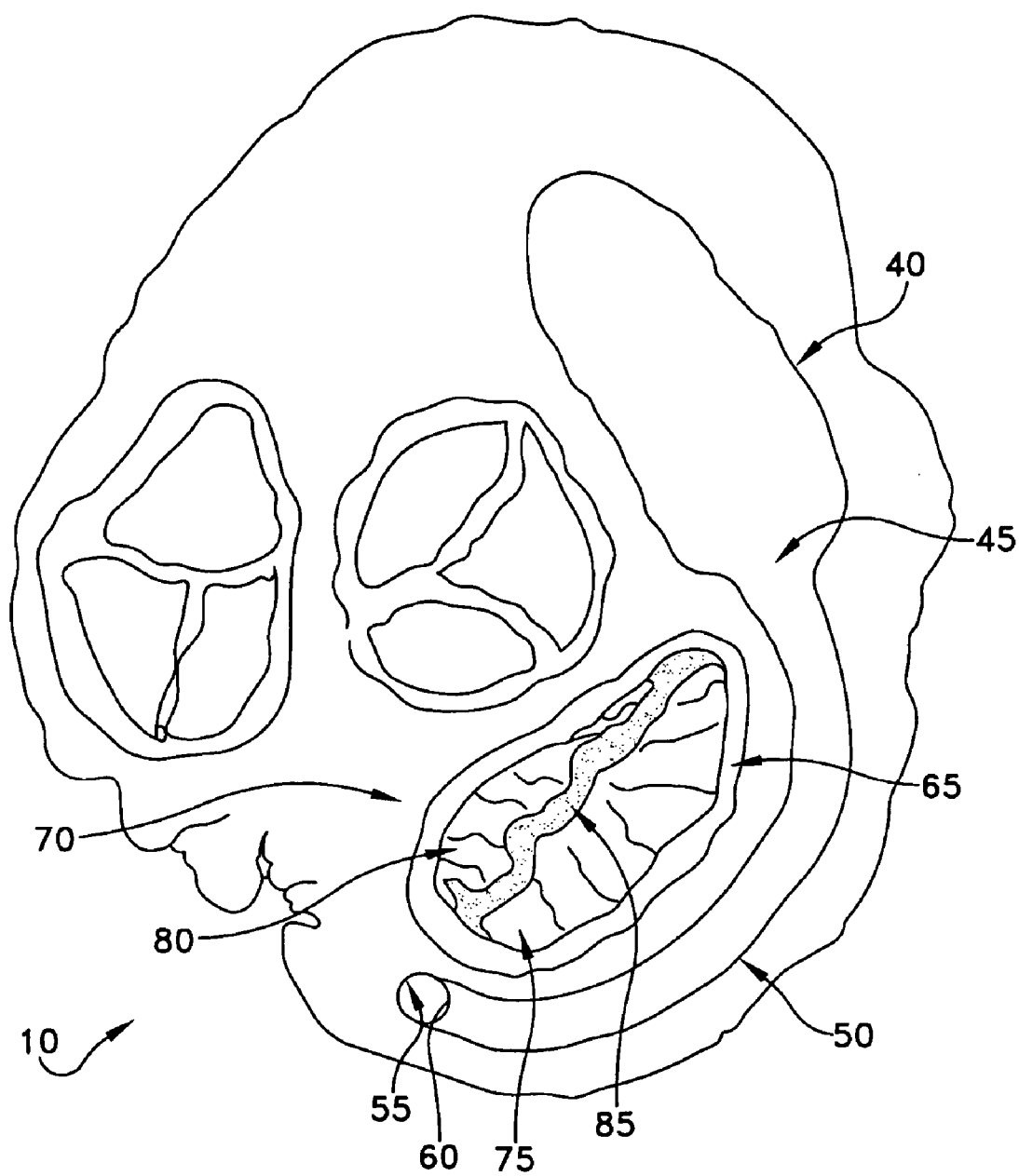
FIG. 2 is a schematic view of portions of the human heart.

Looking now at FIGS. 1 and 2, there are shown aspects of the cardiovascular system 5 of a patient. More particularly, cardiovascular system 5 generally comprises the heart 10, the superior vena cava 15, the right subclavian vein 20, the left subclavian vein 25, the jugular vein 30 and the inferior vena cava 35. Superior vena cava 15 and inferior vena cava 35 communicate with the heart's right atrium 40. The coronary ostium 45 leads to coronary sinus 50. At the far end 55 (FIG. 2) of coronary sinus 50, the vascular structure leads to the vertically-descending anterior interventricular vein ("AIV") 60 (FIGS. 1 and 2). For the purposes of the present invention, it can generally be convenient to consider the term "coronary sinus" to mean the vascular structure extending between coronary ostium 45 and AIV 60.

As seen in FIG. 2, between coronary ostium 45 and AIV 60, coronary sinus 50 generally extends substantially adjacent to the posterior perimeter of the annulus 65 of the mitral valve 70. Mitral valve 70 comprises a posterior leaflet 75 and an anterior leaflet 80. In the case of a regurgitant mitral valve, posterior leaflet 75 and anterior leaflet 80 will generally fail to properly coapt at systole, thereby leaving an intervening gap 85 which can permit the undesired regurgitation to occur.

Annuloplasty Device in General

Figure 3:
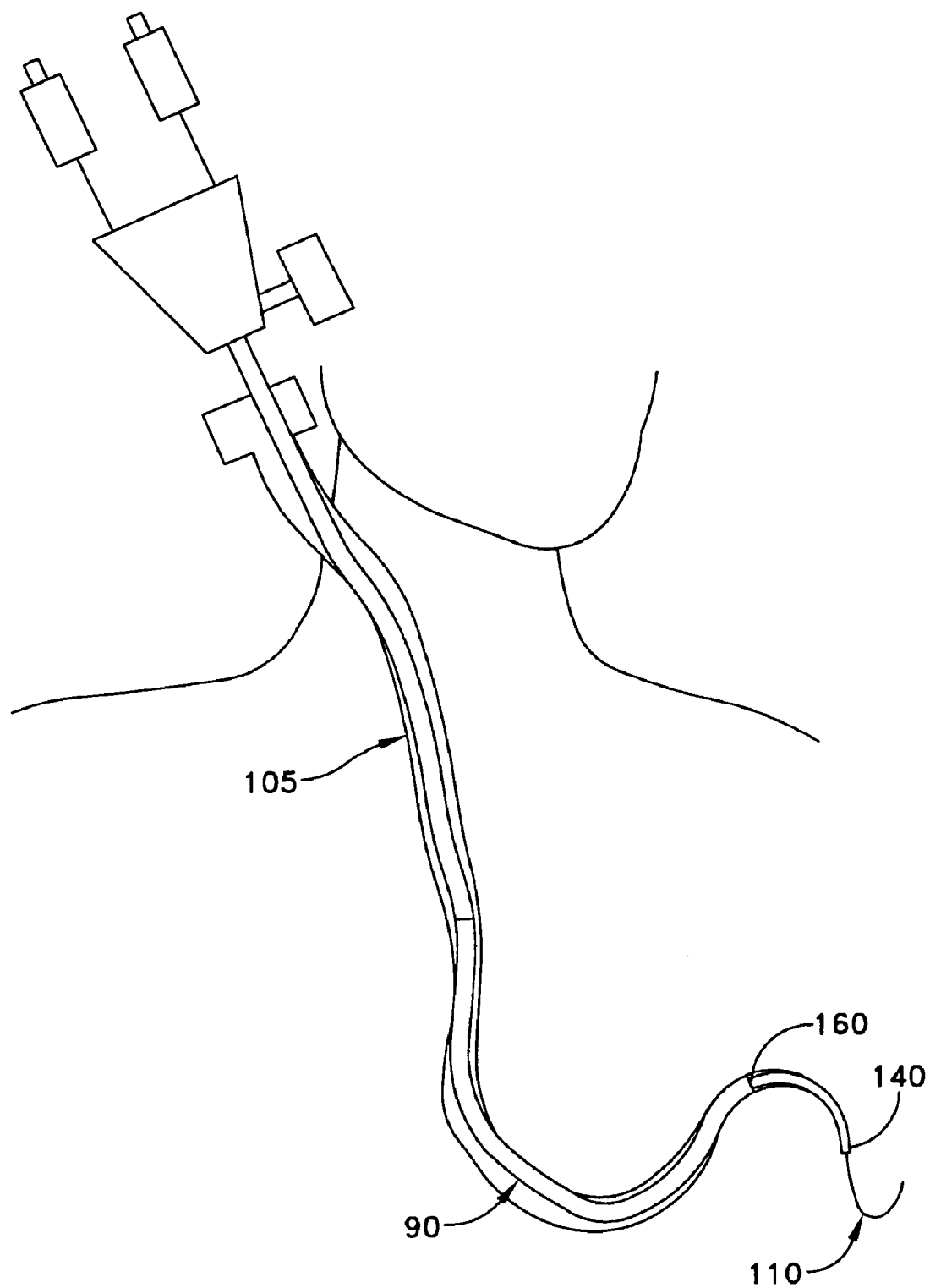
FIG. 3 is a schematic view showing a novel annuloplasty device disposed in a patient's anatomy.
Figure 4:
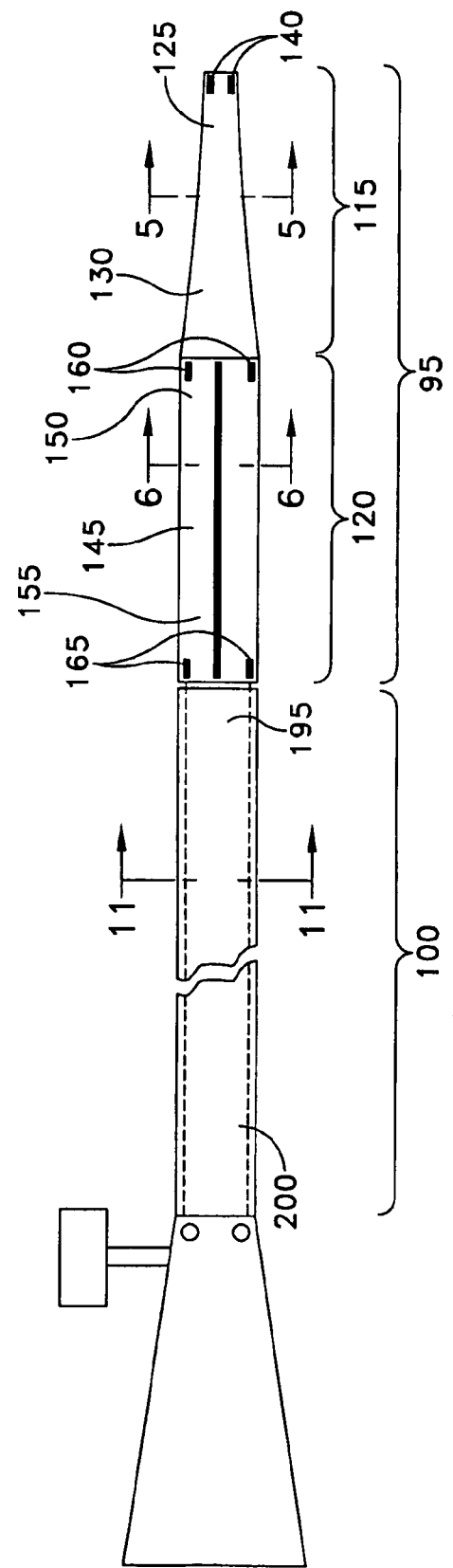
FIG. 4 is a schematic view showing a preferred construction for the annuloplasty device.
Figure 6:
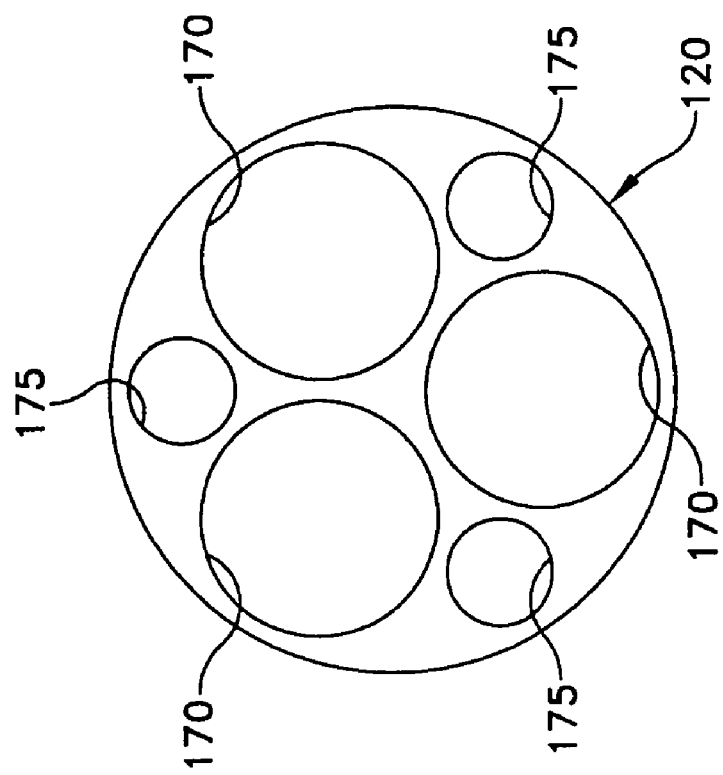
FIGS. 5 and 6 are cross-sectional views taken along lines 5—5 and 6—6 of FIG. 4.
Figure 5:
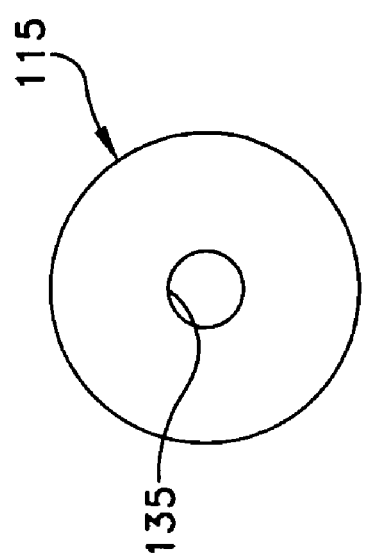

Looking next at FIGS. 3 and 4, there is shown an annuloplasty device 90 which comprises one preferred form of the present invention. Annuloplasty device 90 comprises an implant body 95 (FIG. 4) for therapeutically remodeling the mitral annulus, and a catheter shaft 100 for delivering implant body 95 to the therapy site. A standard introducer sheath 105 (FIG. 3) and a guidewire 110 may be used to introduce annuloplasty device 90 into the coronary sinus of the patient.

Implant Body

Looking next at FIGS. 3–6, in one preferred form of the present invention, implant body 95 comprises a lead section 115 and a treatment section 120.

Lead section 115 comprises a distal end 125 and a proximal end 130. Lead section 115 is preferably tapered along its length, having a narrower distal tip and increasing in diameter as it extends in the proximal direction, such that lead section 115 may facilitate distal movement of implant body 95 through vascular structures. Lead section 115 includes at least one lumen 135 (FIG. 5) extending from its distal end to its proximal end. Lumen 135 facilitates device delivery over guidewire 110 using standard percutaneous delivery techniques, as will hereinafter be discussed in further detail.

Lead section 115 is preferably formed out of a relatively soft, flexible material, e.g., a low durometer silicone rubber, and is sized so that when its proximal end 130 is located at the junction of the coronary sinus and the anterior interventricular vein (AIV), its distal end 125 may be received down the AIV. Preferably one or more radiopaque markers 140 (FIGS. 3 and 4) are located at or near the distal end 125 of lead section 115, so that the location of distal end 125 can be visualized under fluoroscopy or the like.

Treatment section 120 comprises a carrier 145 having a distal end 150 and a proximal end 155. The distal end 150 of carrier 145 is secured to the proximal end 130 of lead section 115, whereby lead section 115 can provide a relatively gentle, atraumatic introduction for treatment section 120 as annuloplasty device 90 is advanced through a vascular structure. Preferably one or more radiopaque markers 160 (FIGS. 3 and 4) are located at or near the distal end 150 of treatment section 120, and one or more radiopaque markers 165 are located at or near the proximal end 155 of treatment section 120, so that the location of treatment section 120 can be visualized under fluoroscopy or the like.

Carrier 145 comprises at least one, and preferably a plurality, of working lumens 170 (FIG. 6) extending from its proximal end 155 toward its distal end 150. The working lumens 170 may all have the same diameter as one another or they may have different diameters from one another. In one preferred construction, three identical working lumens 170, equally disposed about the center axis of carrier 145, extend substantially all the way from the proximal end 155 of carrier 145 to the distal end 150 of carrier 145.

Carrier 145 also comprises at least one, and preferably a plurality, of auxiliary lumens 175 (FIG. 6) extending from its proximal end 155 toward its distal end 150. The auxiliary lumens 175 may all have the same diameter as one another or they may have different diameters from one another. Furthermore, one or more of the auxiliary lumens 175 may have the same diameter as one or more of the working lumens 170. In one preferred construction, three identical auxiliary lumens 175, equally disposed about the center axis of carrier 145 and having a diameter less than the diameter of working lumens 170, extend substantially all the way from the proximal end 155 of carrier 145 to the distal end 150 of carrier 145.

At least one of the working lumens 170 and/or the auxiliary lumens 175 communicates with the at least one lumen 135 (FIG. 5) extending continuously through lead section 115, whereby to facilitate device delivery over guidewire 110 using standard percutaneous delivery techniques, as will hereinafter be discussed in further detail. In one preferred construction, one of the working lumens 170 in carrier 145 communicates with one lumen 135 extending through lead section 115.

Carrier 145 is preferably formed out of a relatively flexible material, such that carrier 145 can be advanced into the coronary sinus of a patient without causing a significant change to the natural geometry of the coronary sinus, as will hereinafter be discussed. In addition, carrier 145 is preferably formed out of a relatively low friction material, such that carrier 145 can be advanced easily through the vascular system of a patient, and such that rods, wires and the like can be easily advanced into, and easily withdrawn from, lumens 170 and 175 of carrier 145. In one preferred embodiment, carrier 145 is formed out of Teflon.

Working lumens 170 are intended to selectively receive straightening rods so as to therapeutically remodel the mitral annulus, as will hereinafter be discussed. One preferred form of straightening rod is the straightening rod 180 shown in FIG. 7.

Figure 7:
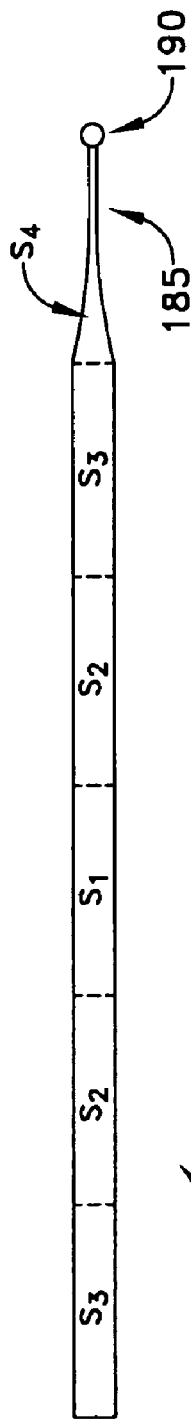
Figure 8:
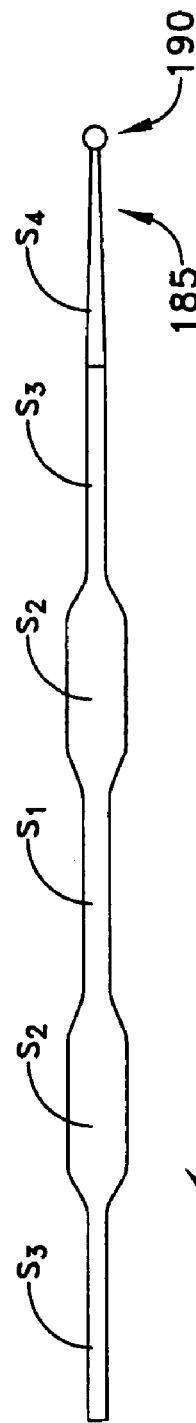
Figure 9:
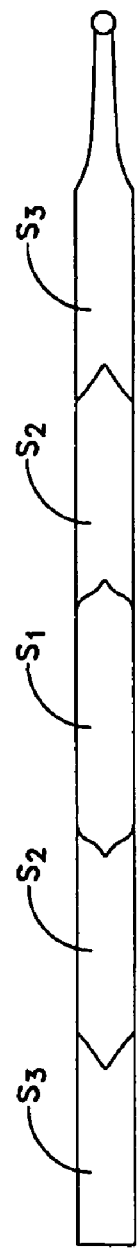

Looking now at FIGS. 7, 8 and 9, each of the straightening rods 180 is formed so as to be somewhat more rigid than the anatomical tissue surrounding the posterior leaflet of the mitral valve, and each of the straightening rods 180 has a shape somewhat straighter than the shape of the coronary sinus in the vicinity of the posterior leaflet of the mitral valve, and each of the straightening rods 180 has a length, such that when a straightening rod 180 is positioned in a working lumen 170 of carrier 145 while the carrier is positioned in the coronary sinus of a patient adjacent to the posterior leaflet of the mitral valve, that straightening rod will impart a straightening force to the wall of the coronary sinus, whereby to move the posterior annulus anteriorly so as to improve leaflet coaptation and, as a result, reduce mitral regurgitation, as will hereinafter be discussed.

In one preferred form of the invention, each of the straightening rods 180 comprises a substantially straight bar (in an unstressed condition) which is somewhat flexible, such that the bar will elastically apply a straightening force to the wall of the coronary sinus.

Each of the straightening rods 180 may deliver exactly the same straightening force to the wall of the coronary sinus as every other straightening rod, or the straightening rods may be engineered so as to provide differing degrees of straightening force. In one preferred form of the invention, a kit comprising a variety of different straightening rods 180, each providing a different degree of straightening force, is provided for appropriate selection by the doctor. Differences in straightening force may be achieved through differences in rod diameters, differences in rod length, differences in rod composition, etc.

And in one preferred form of the invention, each of the straightening rods 180 applies a force to the wall of the coronary sinus which is, by itself, adequate to move the mitral annulus only a fraction of the total distance ultimately desired to reduce mitral regurgitation. In this form of the invention, additional straightening rods 180 may be deployed in carrier 145 to supply additional straightening force to the mitral annulus; and/or additional straightening rods may be deployed in one or more of the auxiliary lumens 175 to supply additional straightening force to the mitral annulus; and/or additional straightening elements may be incorporated in, or on, or around, carrier 145 so as to supply additional straightening force to the mitral annulus. By way of example but not limitation, additional straightening rods may be molded into the body of carrier 145 in the regions between working lumens 170 and auxiliary lumens 175; and/or an external slat or shell or tube may be formed on the exterior surface of carrier 145.

Additionally, or as an alternative to the foregoing, the apparatus may be constructed so as to apply an elastic straightening force to the mitral annulus, such that a force which initially moves the mitral annulus only a fraction of the total distance ultimately desired to reduce mitral regurgitation, may dynamically work its therapeutic effect over time as the coronary tissue remodels.

In one preferred form of the invention, each of the straightening rods 180 comprises a multizone bar having regions of differing flexibility. As a result, different portions of the mitral annulus may be reconfigured with differing amounts of force so as to achieve improved leaflet coaptation.

In one particularly preferred form of the invention, each of the straightening rods 180 comprises a "5-zone bar" similar to the 5-zone bar disclosed in the aforementioned U.S. patent application Ser. Nos. 10/446,470; 60/489,549; and 60/562,958, e.g., and looking now at FIG. 7, each of the straightening rods 180 comprises a central region (or hinge) $S_1$ having a selected degree of flexibility; extension segments (or arms) $S_2$ having a lower degree of flexibility than central region $S_1$; and end segments (or feet) $S_3$ having a higher degree of flexibility than central region $S_1$. This 5-zone bar has been found to be a particularly advantageous construction inasmuch as (1) the 5-zone bar tends to center itself in the coronary sinus in position about the posterior leaflet of the mitral valve, in a sort of "macroelastic energy well", whereby to minimize undesirable longitudinal bar migration; (2) the 5-zone bar tends to improve leaflet coaptation by reducing the distended mitral valve's anterior-to-posterior dimension without increasing the valve's commissure-to commissure dimension, whereby to minimize the creation of undesirable "side jets"; and (3) the 5-zone bar has also been found to accommodate patient-to-patient anatomical variations extremely well.

In practice, each of the straightening rods 180 is also preferably formed with a tapered distal end 185 (FIG. 7) terminating in an atraumatic ball tip 190, such that the straightening rod 180 can be easily advanced from a location outside the body into a working lumen 170 of carrier 145 when the carrier 145 is disposed in the coronary sinus of a patient. As a consequence of the foregoing construction, each of the straightening rods 180 effectively has an additional distal end segment $S_4$ having a degree of flexibility even higher than the flexibility of the aforementioned end segments $S_3$.

If desired, one or more of the straightening rods 180 may be formed out of a single piece of material (e.g., Nitinol), with the regions of differing flexibility $S_1$, $S_2$, $S_3$ and $S_4$ being provided by different rod diameters (see, for example, the construction shown in FIG. 8); and/or straightening rods 180 may combine two or more different materials (e.g., stainless steel and Nitinol, etc.) in a composite construction (see, for example, the construction shown in FIG. 9 where the straightening rod comprises alternating sections of Nitinol and stainless steel, or the constructions shown in FIGS. 10 and 10A, where the straightening rod comprises concentric arrangements of Nitinol and stainless steel), etc.

Catheter Shaft

Catheter shaft 100 (FIG. 4) serves to deliver implant body 95 to the therapy site. Catheter shaft 100 comprises a distal end 195 and a proximal end 200. The distal end 195 of catheter shaft 100 engages the proximal end 155 of implant body 95 while catheter shaft 100 is delivering implant body 95 to the therapy site and, in some forms of the invention, is preferably selectively separable from the proximal end 155 of implant body 95 at some point thereafter. To this end, and as will hereinafter be discussed in further detail, implant body 95 may be formed separate from catheter shaft 100 and be removably secured thereto, or implant body 95 may be formed integral with catheter shaft 100 and be thereafter selectively separable therefrom (e.g., such as by cutting).

Catheter shaft 100 comprises an elongated structure which is sufficiently long, and is formed out of a material which is sufficiently flexible, such that catheter shaft 100 may be used to advance implant body 95 through the vascular system of a patient to the coronary sinus. By way of example but not limitation, catheter shaft 100 may have a length and flexibility such that it can be used to advance implant body 95 from an access point in the jugular vein in the neck or the right or left subclavian vein in the torso, down that access vein, down the superior vena cava, through the right atrium of the heart, and then into the coronary sinus.

Figure 11:
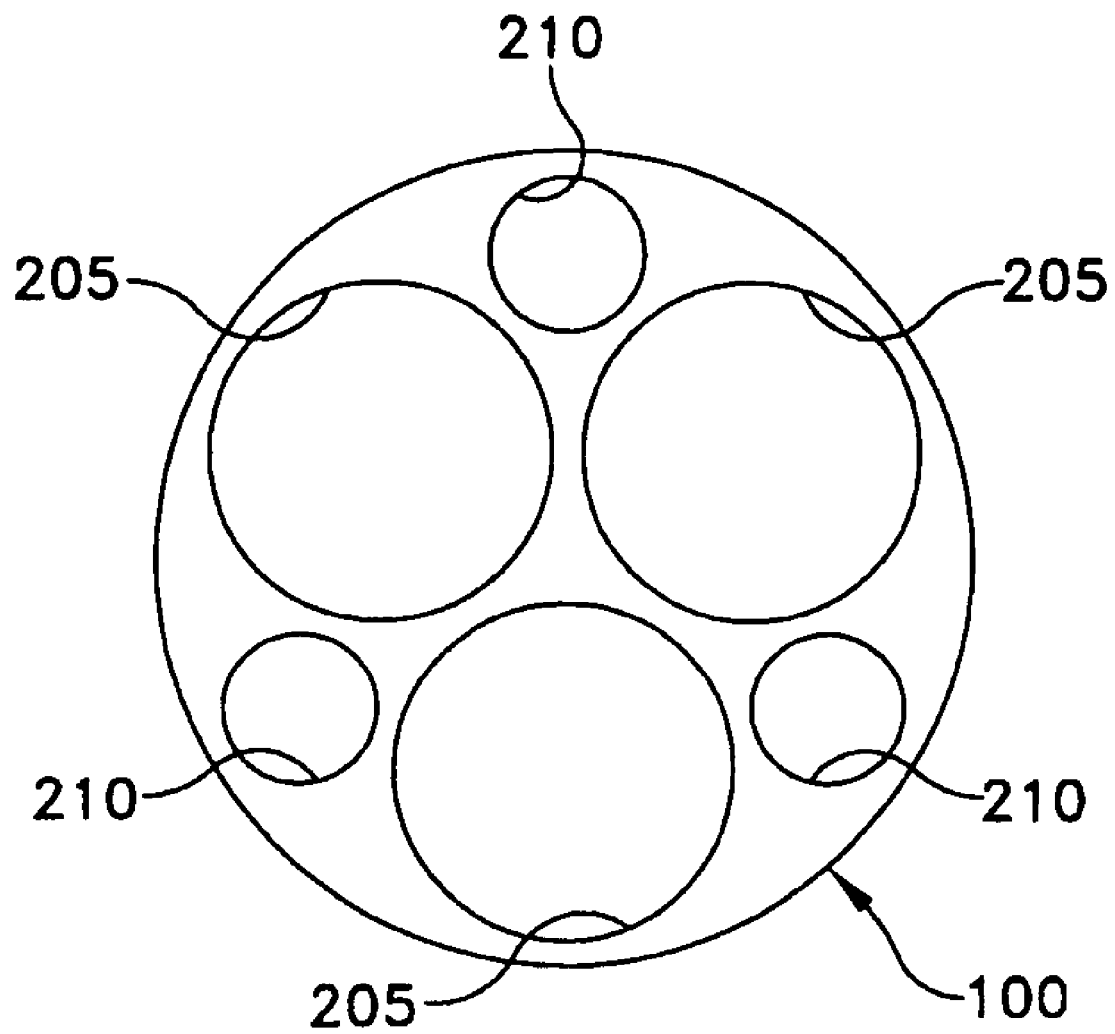
FIG. 11 is a cross-sectional view taken along line 11—11 of FIG. 4.

Looking next at FIGS. 4 and 11, catheter shaft 100 comprises at least one, and preferably a plurality, of working lumens 205. Working lumens 205 open on the distal end 195 of catheter shaft 100, extend completely through catheter shaft 100, and open on the proximal end 200 of catheter shaft 100. Working lumens 205 provide access to the working lumens 170 in carrier 145 and, to this end, the working lumens 205 in catheter shaft 100 are preferably equal in number to, and aligned with, the working lumens 170 provided in carrier 145.

Catheter shaft 100 also comprises at least one, and preferably a plurality, of auxiliary lumens 210. Auxiliary lumens 210 open on the distal end 195 of catheter shaft 100, extend completely through catheter shaft 100, and open on the proximal end 200 of catheter shaft 100. Auxiliary lumens 210 provide access to the auxiliary lumens 175 in carrier 145 and, to this end, the auxiliary lumens 210 in catheter shaft 100 are preferably equal in number to, and aligned with, the auxiliary lumens 175 provided in carrier 145.

Use

Annuloplasty device 90 is preferably used as follows.

Figure 12:
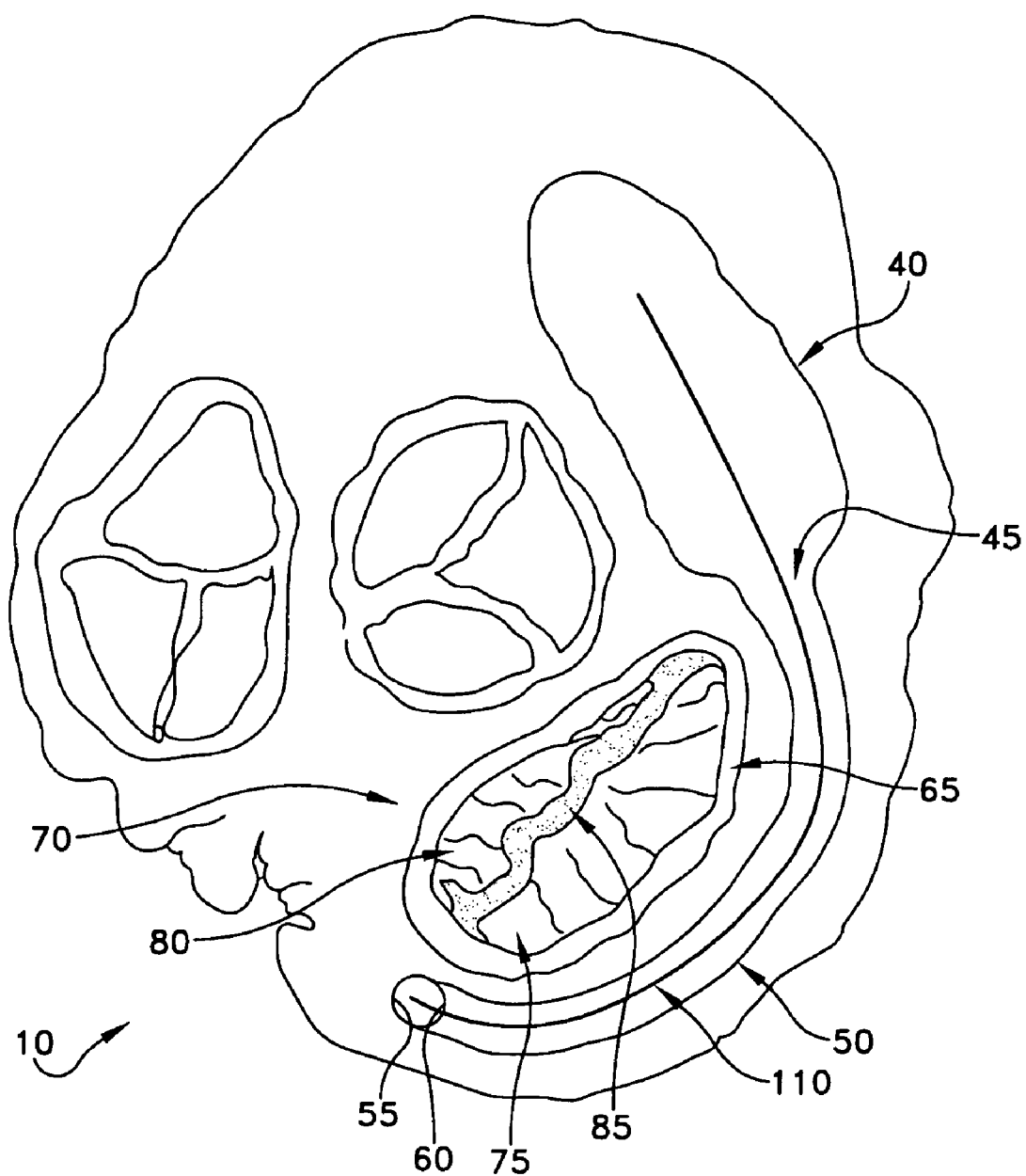
FIGS. 12–14 are a series of views illustrating use of the novel annuloplasty device to reduce mitral regurgitation.

First, a standard introducer sheath 105 (FIG. 3) is introduced into the vascular system of the patient and advanced to the coronary ostium. By way of example but not limitation, this may be accomplished by inserting the introducer sheath into the jugular vein of the patient (or the right or left subclavian vein of the patient), advancing it down the superior vena cava, through the right atrium of the heart, and then into the mouth of the coronary ostium. Then a guidewire 110 is advanced through the standard introducer sheath 105 and into the coronary sinus (FIG. 12). Next, annuloplasty device 90 is loaded onto the guidewire 110. Where annuloplasty device 90 is constructed so that implant body 95 and catheter shaft 100 are formed integral with one another, annuloplasty device 90 may be loaded as a unit onto guidewire 110. Where annuloplasty device 90 is constructed so that implant body 95 and catheter shaft 100 are formed separate from one another, implant body 95 and catheter shaft 100 may be united before being loaded onto guidewire 110, or implant body 95 and catheter shaft 100 may be separately loaded onto the guidewire 110 and thereafter be brought together. Regardless of when implant body 95 and catheter shaft 100 are united (i.e., during manufacture, prior to loading onto guidewire 110 or after loading onto guidewire 110), implant body 95 and catheter shaft 100 are united so that the working lumens 170 in carrier 145 are aligned with the working lumens 205 in catheter shaft 100, and so that the auxiliary lumens 175 in carrier 145 are aligned with the auxiliary lumens 210 in catheter shaft 100. Annuloplasty device 90 is preferably loaded onto guidewire 110 by passing an aligned pair of working lumens 170, 205 over the proximal end of guidewire 1110 and then advancing the annuloplasty device 90 distally along the guidewire. Alternatively, annuloplasty device 90 may be loaded onto guidewire 110 by passing an aligned pair of auxiliary lumens 175, 210 over the proximal end of guidewire 110 and then advancing the annuloplasty device 90 distally along the guidewire; or other lumens may be provided in annuloplasty device 90 for loading the annuloplasty device 90 onto the guidewire.

Figure 13:
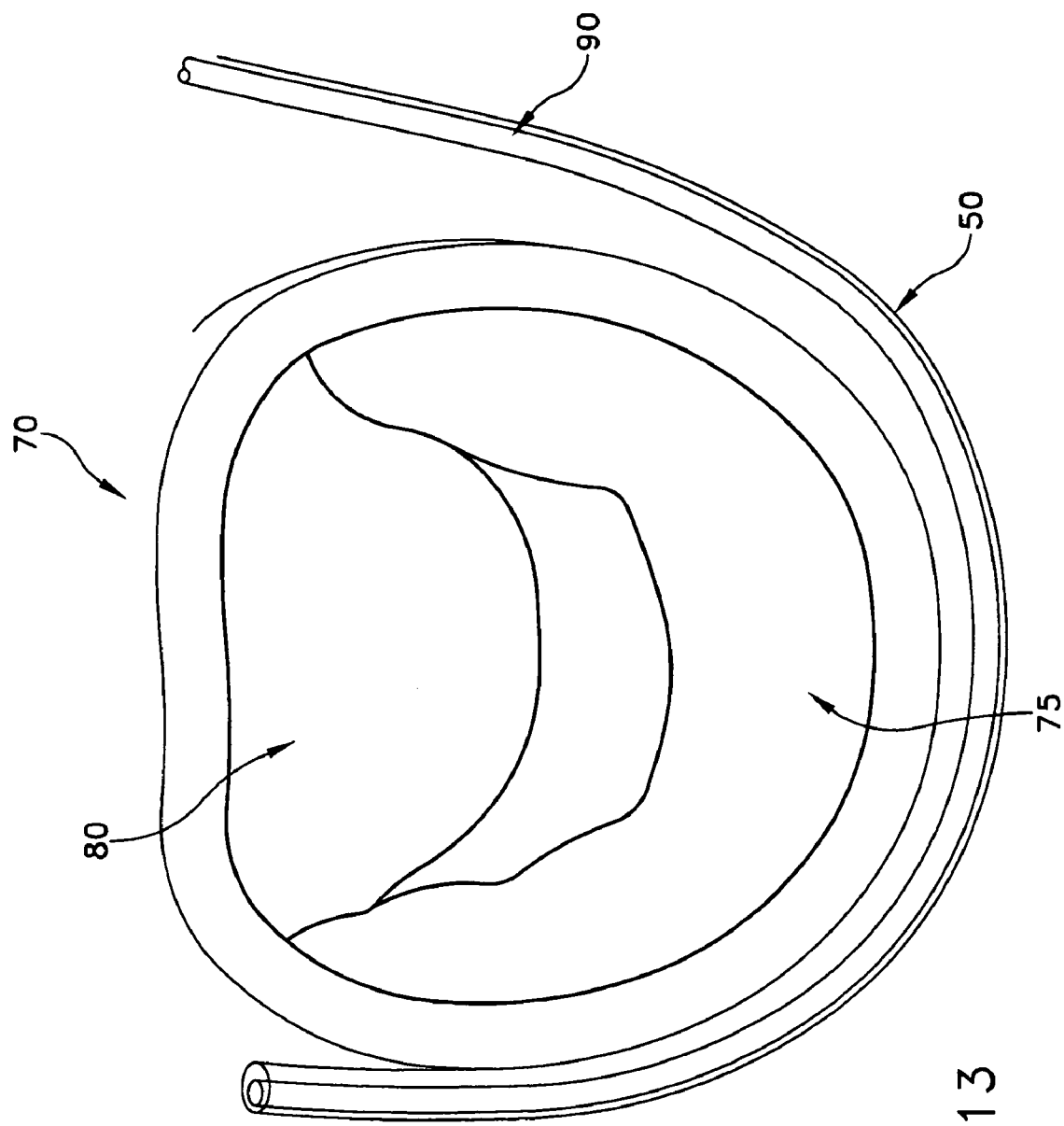

Next, annuloplasty device 90 is advanced distally down the guidewire 110 until its treatment section 120 is positioned adjacent to the posterior leaflet of the mitral valve, with lead section 115 extending down the AIV, and with the junction of treatment section 120 and lead section 115 being located at the junction of the coronary sinus and the AIV (FIGS. 3 and 13). Radiopaque markers 140, 160 and/or 165 may be used to help position annuloplasty device 90 under fluoroscopy or the like.

Preferably, there are no straightening rods 180 disposed in the working lumens 170 of treatment section 120 while annuloplasty device 90 is being advanced to the therapy site. As a result, inasmuch as carrier 145 is formed out of a relatively flexible material, carrier 145 will be able to readily flex as the annuloplasty device 90 is advanced through the vascular system of the patient, thereby facilitating device advancement. This is a significant advantage of the present invention, since it allows the annuloplasty device to be deployed with a minimum of tissue trauma and with a reduced risk of device kinking.

Inasmuch as carrier 145 is formed out of a relatively flexible material, it can be desirable to insert obturators into any unused working lumen pairs 170, 205 prior to advancement of annuloplasty device 90 down guidewire 110. This can help keep unused lumens open and, particularly where carrier 145 is bending, help prevent a straightening rod from plunging through the side wall of the carrier when straightening rods are thereafter advanced into the carrier. By way of example, where a carrier 145 has three working lumens 170, obturators located in two of the working lumens 170 can provide "rails" for guiding the insertion of a straightening rod into the remaining (i.e., third) working lumen. However, in this respect it should also be appreciated that it is generally desirable that such obturators be as flexible as possible, such that they can keep unused working lumen pairs 170, 205 open without imposing a significant resistance to device flexing and/or advancement.

Similarly, obturators may be inserted into any unused auxiliary lumen pairs 175, 210 prior to advancement of the annuloplasty device 90 down guidewire 110.

Once annuloplasty device 90 has been advanced into the vascular system of the patient so that its treatment section 120 is positioned in the coronary sinus adjacent to the posterior leaflet of the mitral valve, guidewire 110 may be withdrawn. Alternatively, to the extent that the lumens occupied by guidewire 110 are not needed for another purpose, guidewire 110 may be left in place. This can be advantageous, since guidewire 110 can provide support for its host lumens (e.g., a working lumen pair 170, 205) while the guidewire extends through annuloplasty device 90.

Next, one or more straightening rods 180 is advanced into the working lumens 170 of carrier 145. This is preferably done by first advancing the straightening rod 180 through a working lumen 205 of catheter shaft 100 and then into a working lumen 170 of carrier 145. To the extent that the working lumens 205 and 170 are filled with an obturator or guidewire during insertion of annuloplasty device 90 into the coronary sinus, the same is withdrawn prior to inserting the straightening rod.

Figure 14:
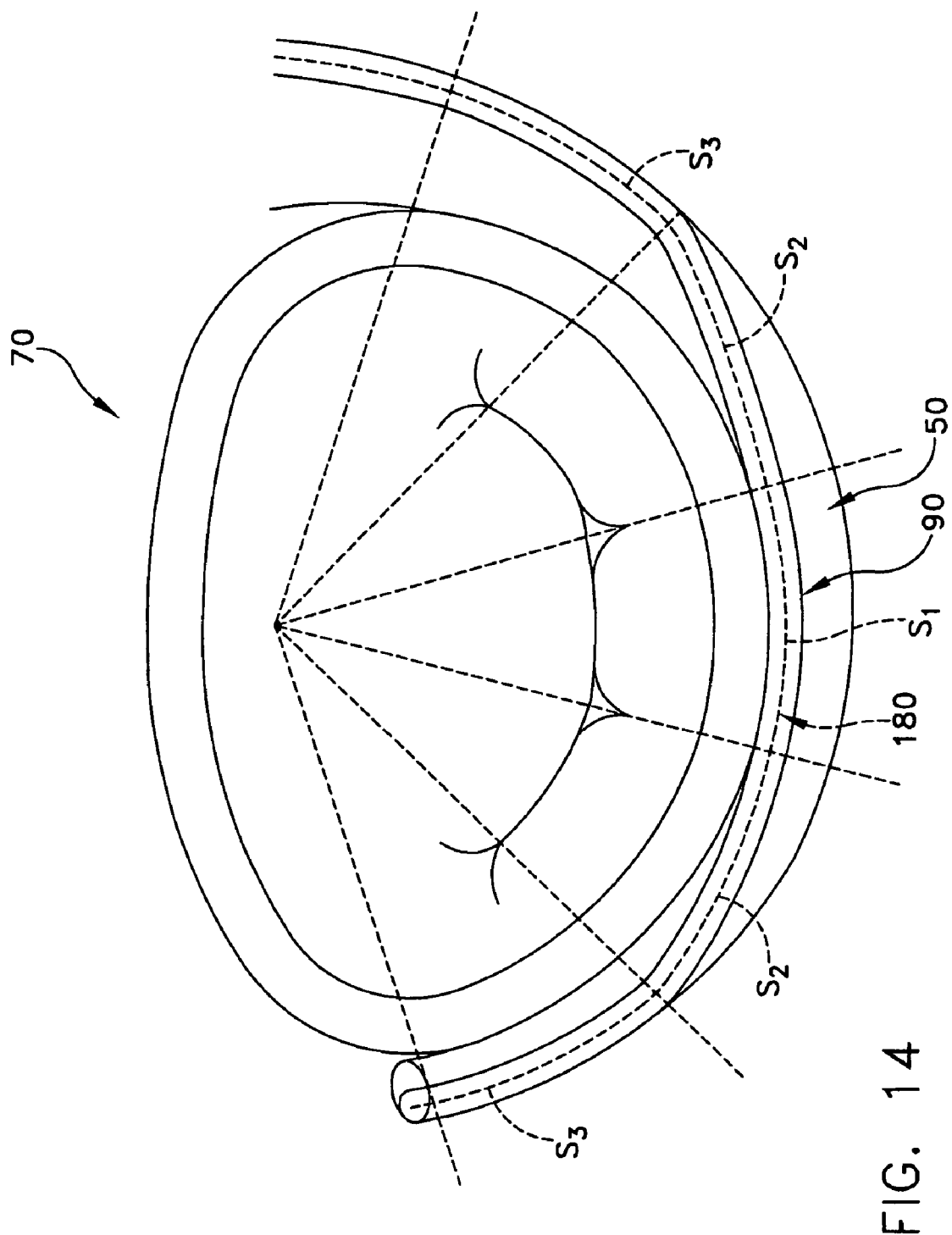

As each straightening rod 180 is inserted into a working lumen 170 of carrier 145, the carrier becomes progressively stiffer and hence straighter, incrementally remodeling the geometry of the distended mitral valve so as to urge its posterior leaflet anteriorly, whereby to reduce mitral regurgitation (FIG. 14). As each successive straightening rod 180 is inserted into a working lumen 170 of carrier 145, the degree of mitral valve regurgitation is observed, with the process continuing until the degree of regurgitation is minimized. In essence, with the straightening rods 180 being inserted into carrier 145 while the carrier is disposed in the coronary sinus, implant body 95 is assembled in situ. This approach provides a number of significant advantages. Among other things, the serial insertion of the straightening rods into carrier 145 allows the therapeutic treatment to be applied in a "stepwise fashion", thereby allowing "fine tuning" of the tissue reconfiguration so as to enable optimal treatment. In this respect it is noted that straightening rods 180 are preferably provided in the form of a kit comprising a variety of different straightening rods 180, each providing a different degree of straightening force, whereby to facilitate delivery of the optimal amount of tissue reconfiguration force. See, for example, FIG. 14A, which shows how three different straightening rod lengths, each provided in six different stiffnesses, can yield a selection of eighteen different straightening forces available to the doctor. Furthermore, since the therapeutic load is imposed on the patient's anatomy incrementally, tissue trauma is reduced. And inasmuch as the invention uses less traumatic apparatus, the system elements can be made simpler and less expensive. Still other advantages of the novel approach of the present invention will be apparent to those skilled in the art in view of the present disclosure.

Furthermore, by forming carrier 145 out of a relatively low friction material, e.g., Teflon, straightening rods 180 will be slidably received in carrier 145 and carrier 145 will be slidably received within coronary sinus 30. As a result, as successive straightening rods 180 are inserted into carrier 145 and the posterior annulus is progressively moved anteriorly, the distal and proximal ends of the apparatus will be free to slide outwardly as needed as the apparatus assumes a straighter configuration.

Figure 14B:
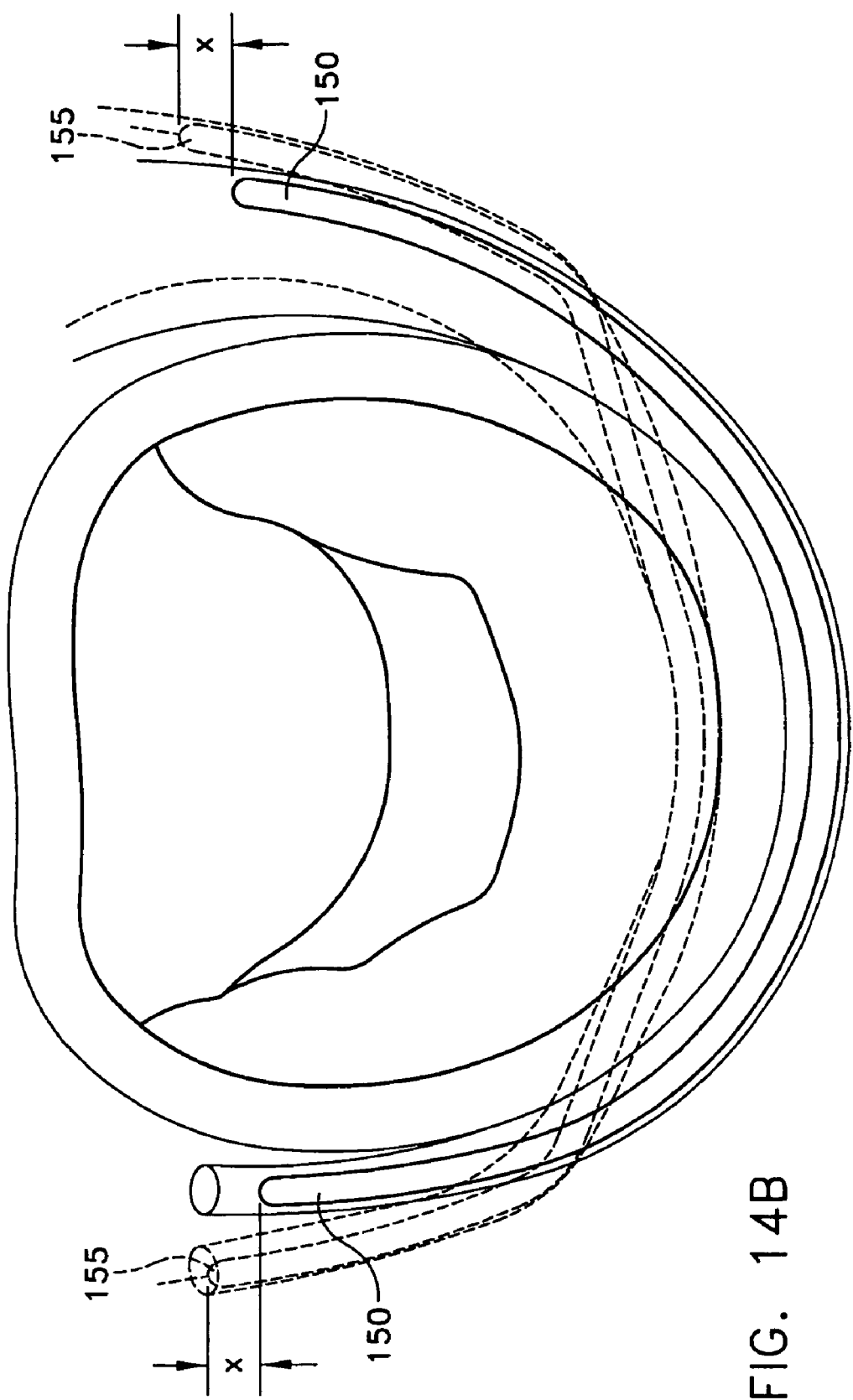
FIG. 14B is a schematic view showing how the annuloplasty device is designed to slip atraumatically vis-à-vis the anatomy as the coronary sinus is straightened so as to reduce mitral regurgitation.

More particularly, and looking now at FIG. 14B, the annuloplasty device's treatment section 120 is shown deployed in the patient's anatomy. As the treatment section 120 transitions from a non-straightening state (solid line) to a straightening state (phantom line) due to the insertion of straightening rods 180, the distal and proximal ends 150 and 155 of treatment section 120 atraumatically slide along the anatomy (i.e., by some distance X) in view of the constant length of the treatment section and the changing shape of the anatomy. By forming carrier 145 out of a relatively low friction material (e.g., Teflon), this device slide can be accommodated relatively atraumatically. Indeed, inasmuch as the anatomy is reconfigured incrementally with the insertion of each successive straightening rod, this device slide also incurs incrementally, thereby further reducing tissue trauma.

Additional Preferred Construction Details

Straightening rods 180 are sized and shaped so that they will induce a straightening of the coronary sinus when they are deployed in the coronary sinus. More particularly, each of the straightening rods 180 is formed so as to be somewhat more rigid than the anatomical tissue surrounding the posterior leaflet of the mitral valve, and each of the straightening rods 180 has a shape somewhat straighter than the natural curvature the patient's coronary sinus in the vicinity of the posterior leaflet of the mitral valve, and each of the straightening rods 180 has a length, such that when the straightening rod is disposed in the coronary sinus of the patient, it will impart a straightening force to the coronary sinus, so as to apply an anteriorly-directed force to the posterior leaflet of the mitral valve, whereby to reduce mitral regurgitation.

Significantly, the carrier 145 may be constructed so that it, by itself, applies only a nominal straightening force to the wall of the coronary sinus. This arrangement can be highly advantageous, since it means that a carrier 145 lacking straightening rods 180 can be easily and atraumatically advanced to the therapy site.

And, significantly, each straightening rod 180 need apply only a fraction of the total straightening force which is to be applied to the wall of the coronary sinus, since the cumulative effect of multiple straightening rods 180 may be harnessed. This is also highly advantageous, since it means that each individual straightening rod may be easily and atraumatically advanced to the therapy site.

Also, significantly, by applying the straightening force to the mitral annulus through the use of one or more independently deployed straightening rods, different degrees of straightening force may be applied by using more or less straightening bars, and/or by using more or less rigid straightening bars, etc.

Significantly, by forming each straightening rod 180 out of a resilient material, each straightening rod 180 need only apply a fraction of the force needed to effect substantially complete leaflet coaptation, inasmuch as the straightening rod can dynamically effect leaflet coaptation over time as the tissue progressively remodels. In this respect it should be noted that tissue tends to respond dynamically, so that a flexible bar can be used to progressively drive the tissue closer and closer to a final position, whereby to effect tissue remodeling over a period of time, with the tissue being subjected to less trauma than if the desired tissue remodeling had been induced entirely at one time.

If desired, straightening rods 180 may also be pre-loaded into one or more working lumens 170 of treatment section 120 prior to advancing annuloplasty device 90 into the coronary sinus; or straightening rods 180 may be pre-loaded into one or more working lumens 205 of catheter shaft 100 prior to advancing annuloplasty device 90 into the coronary sinus.

If desired, straightening rods may be inserted into auxiliary lumens 175 of carrier 145 so as to induce the desired straightening of the mitral annulus. This may be done in addition to inserting straightening rods into working lumens 170, or as an alternative to inserting straightening rods into working lumens 170.

In one preferred construction, straightening rods are deployed in both working lumens 170 and auxiliary lumens 175 so as to effect the desired annulus straightening.

And in one particularly preferred construction, the flexibility of the straightening rods in working lumens 170 is coordinated with the flexibility of the straightening rods in auxiliary lumens 175 so as to achieve improved annulus straightening.

Figure 15:
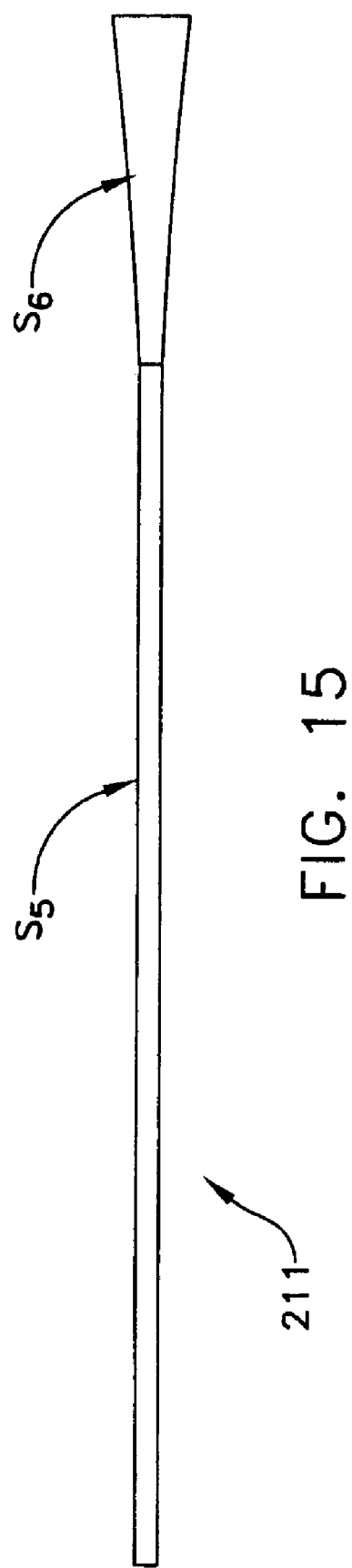
FIG. 15 is a schematic view of an auxiliary straightening rod.

More particularly, and referring now to FIG. 7, it will be recalled that, in one preferred form of straightening rod 180, the distal end segment $S_4$ of straightening rod 180 has a relatively high degree of flexibility, whereby to facilitate endoluminal advancement of the straightening rod to the coronary sinus of the patient. However, this feature also has the effect of reducing the straightening force generated by distal end segment $S_4$, which can adversely affect annulus straightening in this region of the coronary sinus. To this end, and looking now at FIG. 15, there is provided an auxiliary straightening rod 211 which comprises at least a proximal end segment $S_5$ having a first degree of flexibility and a distal end segment $S_6$ having a second, higher degree of flexibility, where the flexibility of distal end segment $S_6$ is coordinated with the flexibility of distal end segment $S_4$ in straightening rod 180 so as to collectively provide a desired annulus straightening force.

Figure 16:
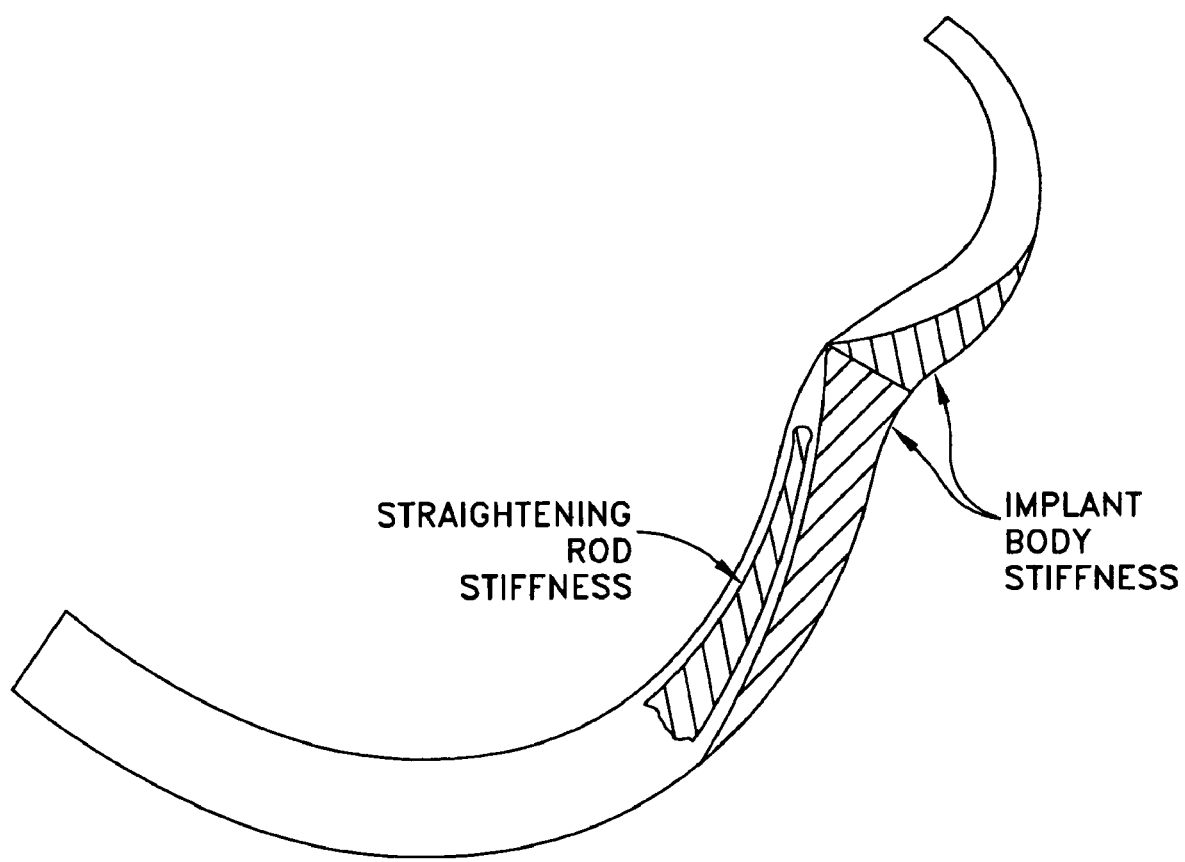
FIG. 16 is a schematic view showing how a straightening rod and an auxiliary straightening rod may have inversely coordinated flexibility gradients.

In one preferred form of the invention, the distal end of auxiliary straightening rod 211 has a flexibility gradient which decreases in the proximal direction, whereby to compensate for the distal end of straightening rod 180, which has a flexibility gradient which increases in the proximal direction. This effect is schematically illustrated in FIG. 16. Such flexibility gradients may be achieved in various ways, e.g., through changes in rod diameter, through the use of more than one construction material, etc.

In one preferred form of the invention, one or more straightening rods 211 are deployed in auxiliary lumens 210 prior to advancing annuloplasty device 90 into the coronary sinus, and one or more straightening rods 180 are thereafter deployed in working lumens 170 after annuloplasty device 90 has been advanced into the coronary sinus.

If desired, straightening rods 180 may be formed out of a material able to accommodate the high strain imposed on straightening rods 180 (e.g., a superelastic metal such as Nitinol), and straightening rods 211 may be formed out of another material able to provide the high strength needed by carrier 145 (e.g., surgical grade stainless steel).

As noted above, it is generally desirable that the straightening rods 180 be inserted into working lumens 170 after annuloplasty device 90 has been advanced into the coronary sinus, whereby to facilitate passage of annuloplasty device 90 into the coronary sinus.

Figure 17:
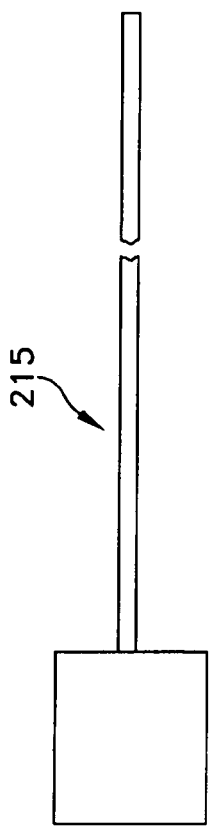
FIGS. 17–21 show various forms of push rods for advancing a straightening rod into an implant body.

In one form of the invention, a simple push rod 215 (FIG. 17) may be used to push a straightening rod 180 through a working lumen 205 in catheter shaft 100 and into a working lumen 170 in treatment section 120.

In some circumstances it may be desirable to remove a straightening rod 180 from a working lumen 170. By way of example but not limitation, it may be necessary or desirable to replace one straightening rod with another straightening rod while treatment section 120 is in the coronary sinus so as to adjust the amount of force applied to the mitral annulus. Or it may be necessary or desirable to remove a deployed annuloplasty device 90 from the coronary sinus, which may in turn make it necessary or desirable to remove a straightening rod 180 from treatment section 120 while the treatment section is located in the coronary sinus. Removal of a straightening rod 180 from treatment section 120 may be accomplished by releasably coupling the proximal end of the straightening rod 180 to the distal end of the push rod which is used to advance that straightening rod.

Figure 18:
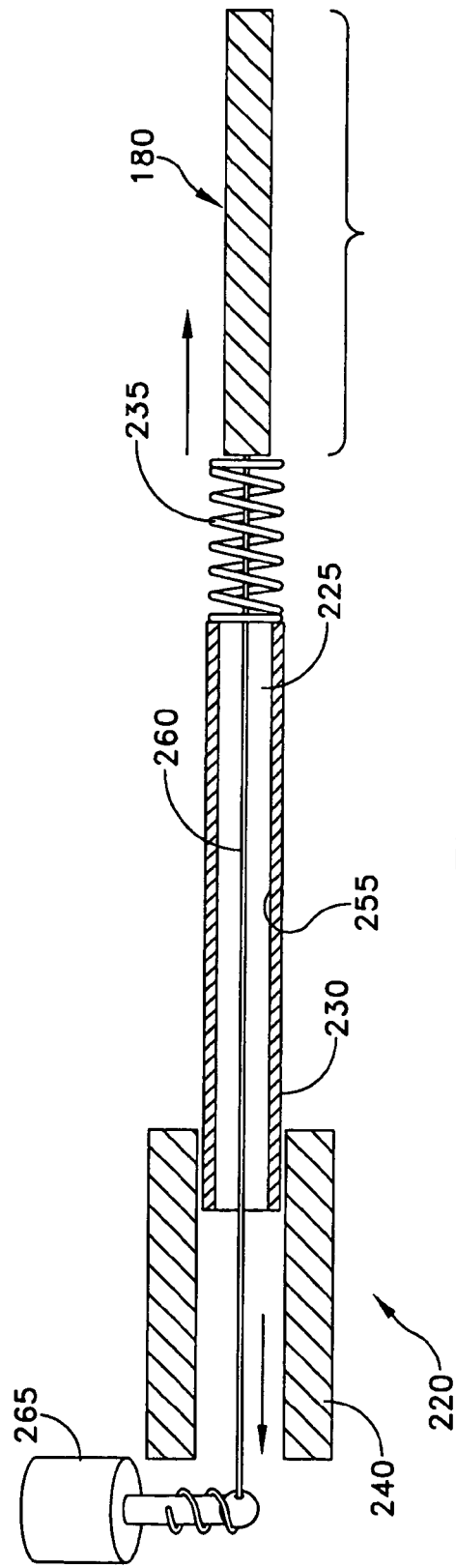

More particularly, and looking now at FIG. 18, there is shown a push rod 220 which is releasably secured to a straightening rod 180. Push rod 220 comprises a distal end 225 and a proximal end 230. A flexible coil spring 235 is preferably formed on the distal end 225 of push rod 220 and engages the proximal end of straightening rod 180. A handle 240 is secured to the proximal end 230 of push rod 220. A central lumen 255 is formed in push rod 220. Central lumen 255 receives a tension wire 260. One end of tension wire 260 is attached to the proximal end of straightening rod 180 and the other end of tension wire 260 is attached to a tensioner 265 carried by handle 240.

In use, while straightening rod 180 is attached to push rod 220, handle 240 is used to advance straightening rod 180 into a working lumen 170 in treatment section 120 or, if desired, retract the straightening rod 180 out of working lumen 170. Thereafter, if and when straightening rod 180 is to be detached from push rod 220, tensioner 265 is used to apply sufficient tension to tension wire 260 so as to break the tension wire free from straightening rod 180, whereupon push rod 220 can be retracted away from annuloplasty device 90 while straightening rod 180 remains in a working lumen 170 in treatment section 120.

Figure 19:
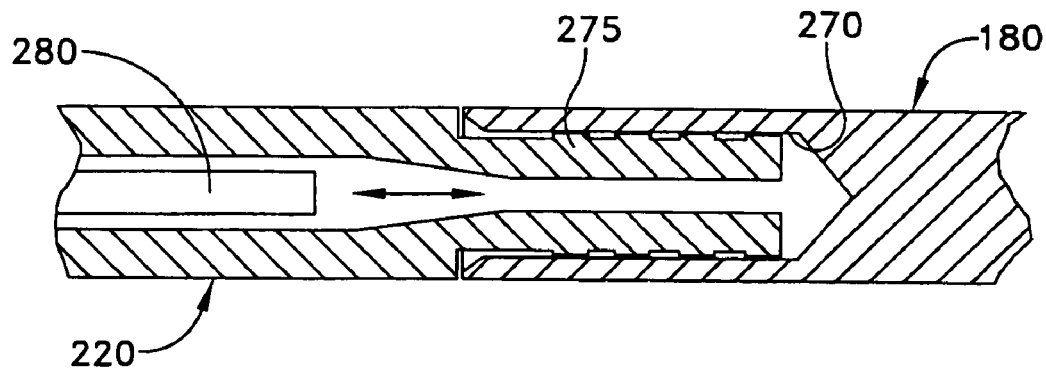
Figure 20:
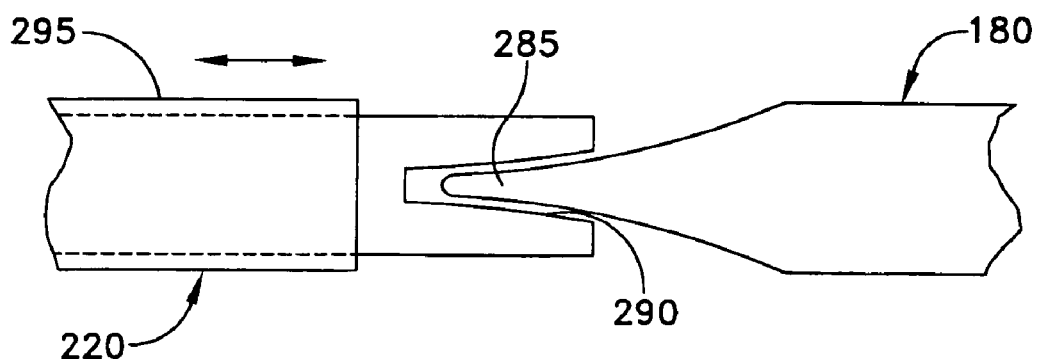
Figure 21:
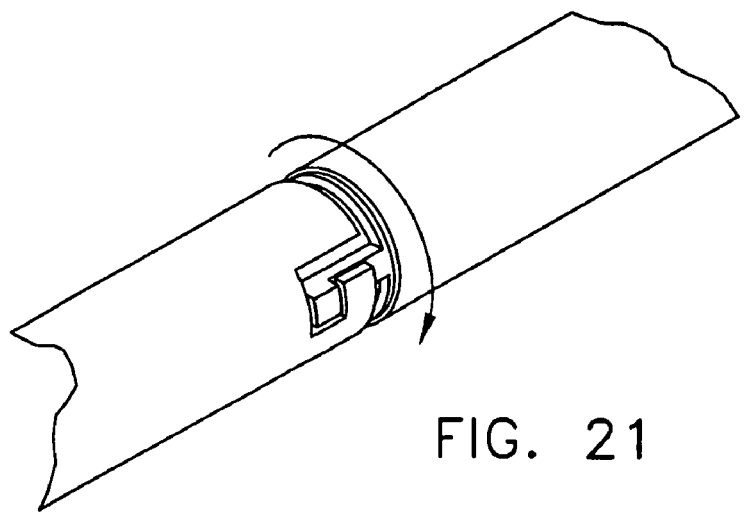

FIGS. 19-21 show additional apparatus for releasably coupling a straightening rod to a push rod. The constructions of FIGS. 19–21 are similar to the construction of FIG. 18 in the sense that they permit the straightening rod 180 to be releasably coupled to the push rod, but they also have the additional advantage that the constructions of FIGS. 19–21 permit a straightening rod to be re-acquired by the push rod after it has been released from the push rod.

Looking next at FIG. 19, there is shown one possible construction for releasably securing a straightening rod 180 to a push rod 220 such that the push rod can subsequently re-acquire the straightening rod. More particularly, with this particular construction, (i) the proximal end of straightening rod 180 includes a recess 270, and (ii) push rod 220 comprises an outer split tube 275 and an inner wedge rod 280. When inner wedge rod 280 is retracted proximally, out of outer split tube 275, outer split tube 275 will assume a relaxed condition such that it can slip in and out of recess 270 without gripping the interior surface of recess 270. However, when outer split tube 275 is placed within recess 270 and inner wedge rod 280 is thereafter advanced distally into outer split tube 275, outer split tube 275 will be forced into a diametrically-expanded condition such that the outer split tube 275 can grip the interior surface of recess 270, whereby to secure straightening rod 180 to push rod 220. Straightening rod 180 may thereafter be released from push rod 220 by retracting inner wedge rod 280 proximally out of outer split tube 275, and then withdrawing push rod 220 away from straightening rod 180.

Looking next at FIG. 20, there is shown another possible construction for releasably securing a straightening rod 180 to a push rod 220. More particularly, with this particular construction, (i) the proximal end of straightening rod 180 includes a male element 285, (ii) the distal end of push rod 220 includes a sprung recess 290, and (iii) a closure tube 295 is concentrically mounted on push rod 220. With this construction, when closure tube 295 is retracted proximally away from spring recess 290, the proximal end of push rod 220 will assume a relaxed, sprung condition such that spring recess 290 can be advanced over, or retracted away from, male element 285 without gripping male element 285. However, when the proximal end of push rod 220 is advanced over male element 285 and closure tube 295 is thereafter advanced distally over spring recess 290, the distal end of push rod 220 will grip male element 285, whereby to secure straightening rod 180 to push rod 220. Straightening rod 180 may thereafter be released from push rod 220 by retracting closure tube 295 away from spring recess 290, and then withdrawing push rod 220 away from straightening rod 180.

Looking next at FIG. 21, there is shown another possible construction for releasably securing a straightening rod 180 to a push rod 220. More particularly, with this particular construction, one or the other of straightening rod 180 and push rod 220 includes one half of a bayonet mount, and the other one of straightening rod 180 and push rod 220 includes the other half of a bayonet mount, whereby straightening rod 180 can be releasably connected to push rod 220.

Still other ways for releasably securing straightening rod 180 to push rod 220 will be apparent to those skilled in the art in view of the present disclosure.

As noted above, catheter shaft 100 (FIG. 4) serves to deliver implant body 95 to the therapy site. The distal end 195 of catheter shaft 100 engages the proximal end 155 of implant body 95 while catheter shaft 100 is delivering implant body 95 to the therapy site and, in some forms of the invention, is preferably separable from the proximal end 155 of implant body 95 at some point thereafter. To this end, implant body 95 may be formed separate from catheter shaft 100 and be removably secured thereto, or implant body 95 may be formed integral with catheter shaft 100 and be thereafter separable therefrom.

In the case where implant body 95 is formed separate from catheter shaft 100 and is removably secured thereto, various arrangements may be used to selectively connect the elements.

Figure 22:
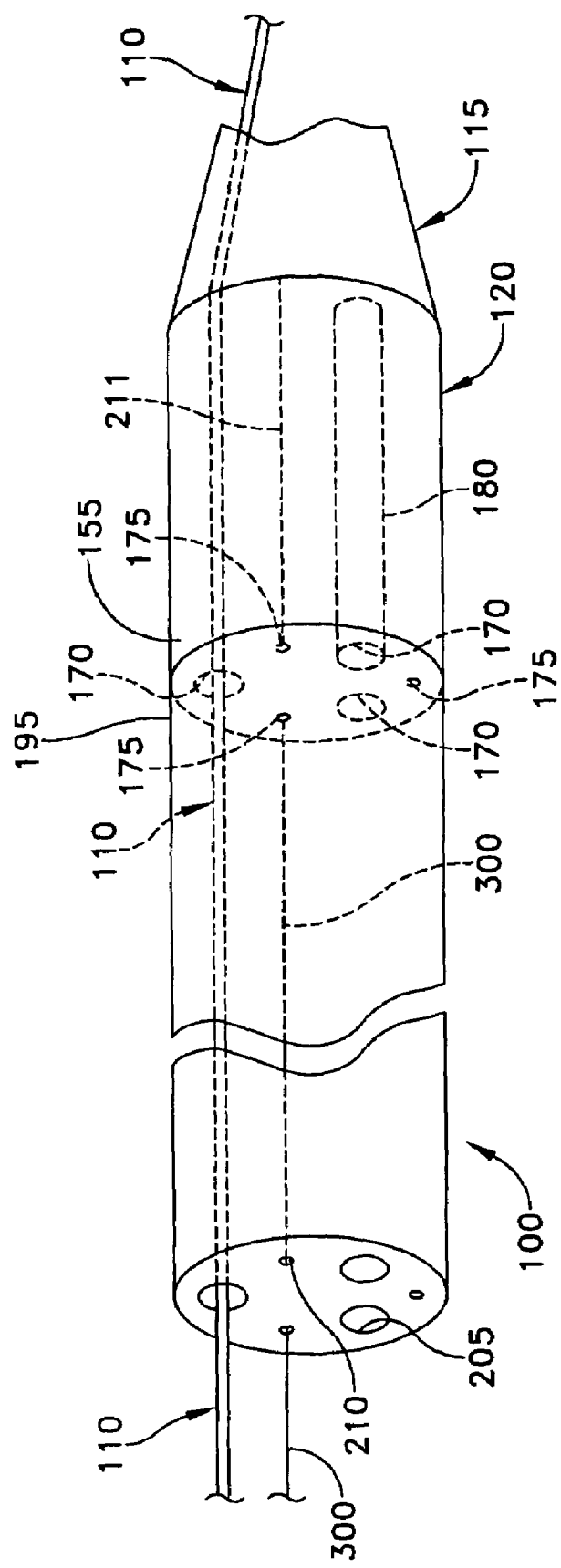
FIG. 22 is a schematic view showing one preferred way for releasably securing an implant body to a catheter shaft.

In one preferred construction, and looking now at FIG. 22, tether lines 300 may be used to releasably secure implant body 95 to catheter shaft 100. More particularly, one or more tether lines 300 have their distal ends fixedly mounted in an auxiliary lumen 175 in treatment section 120, and extend proximally through the catheter shaft's auxiliary lumens 210. Then, by pressing the distal end 195 of catheter shaft 100 against the proximal end 155 of treatment section 120, while pulling tether lines 300 taut, implant body 95 and catheter shaft 100 can be made to behave as a unit. More particularly, when annuloplasty device 90 is to be advanced distally down guidewire 110 to the coronary sinus of the patient, the catheter shaft 100 is used to push implant body 95 distally. If it should become necessary to retract annuloplasty device 90, tether lines 300 may be pulled proximally, pulling implant body 95 proximally (and thus pulling catheter shaft 100 proximally).

Figure 23:
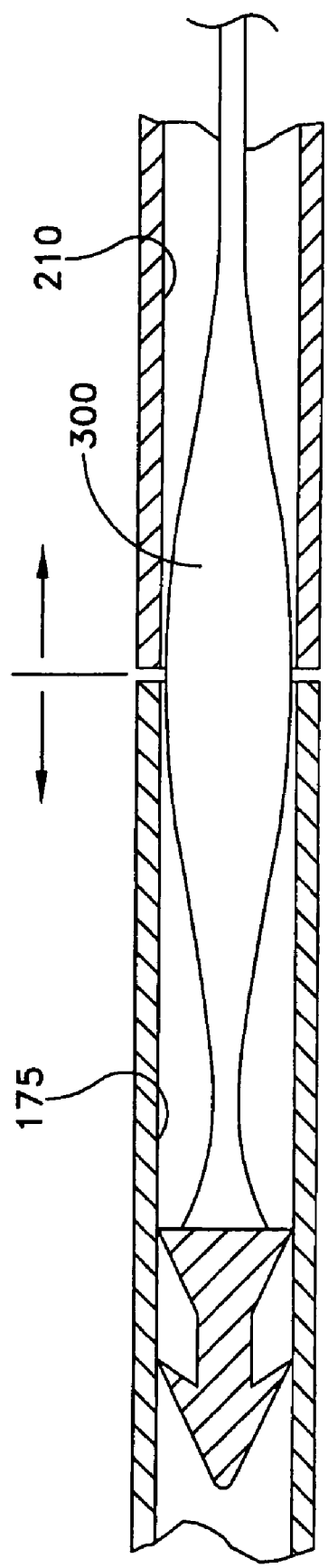
FIG. 23 is a schematic view illustrating one possible way for separating a tether line from the implant body.

If and when implant body 95 is to be left at the treatment site and catheter body 100 withdrawn therefrom, tether lines 300 are pulled proximally while catheter shaft 100 is held stationary, whereupon tether lines 300 will pull free from implant body 95, and then the tether lines 300 and catheter shaft 100 may be withdrawn from the treatment site. FIG. 23 shows one possible construction for achieving this result, where the tether lines 300 are frictionally mounted in auxiliary lumens 175 but withdrawable upon the application of sufficient force (i.e., strong proximal pulling while using catheter shaft 100 to hold implant body 95 in place).

Alternatively, if desired, catheter shaft 100 can be simply backed off tether lines 300, leaving implant body 95 at the treatment site and tether lines 300 extending proximally away from the deployed implant body 95. This approach has the advantage that if it should subsequently become necessary to retrieve implant body 95, tether lines 300 will provide ready access to the deployed implant body 95. This ability to remove implant body 95 from the patient is an important advantage of the present invention.

Furthermore, the presence of exposed tether lines 300 extending proximally from implant body 95 will permit a cap (not shown) to be run down to, and installed on, the proximal end of implant body 95. Such a cap can be used to provide an atraumatic end for implant body 95 and to seal at least some of the interior of implant body 95, whereby to reduce the possibility of coagulation, etc.

It should be appreciated that the implant body 95 described above comprises one preferred form of the elongated body 157, 184 discussed in the aforementioned U.S. patent application Ser. Nos. 10/446,470; 60/489,549; and 60/562,958. As such, it will also be appreciated that implant body 1015 may be deployed alone (e.g., directly against the interior wall of the coronary sinus), or it may be deployed in conjunction with any of the other devices discussed above in connection with the elongated body 157, 184, e.g., it may be deployed within a delivery catheter 106 instead of being advanced over a guidewire, or it may be deployed in conjunction with a stabilizing scaffold, etc.

Figure 24:
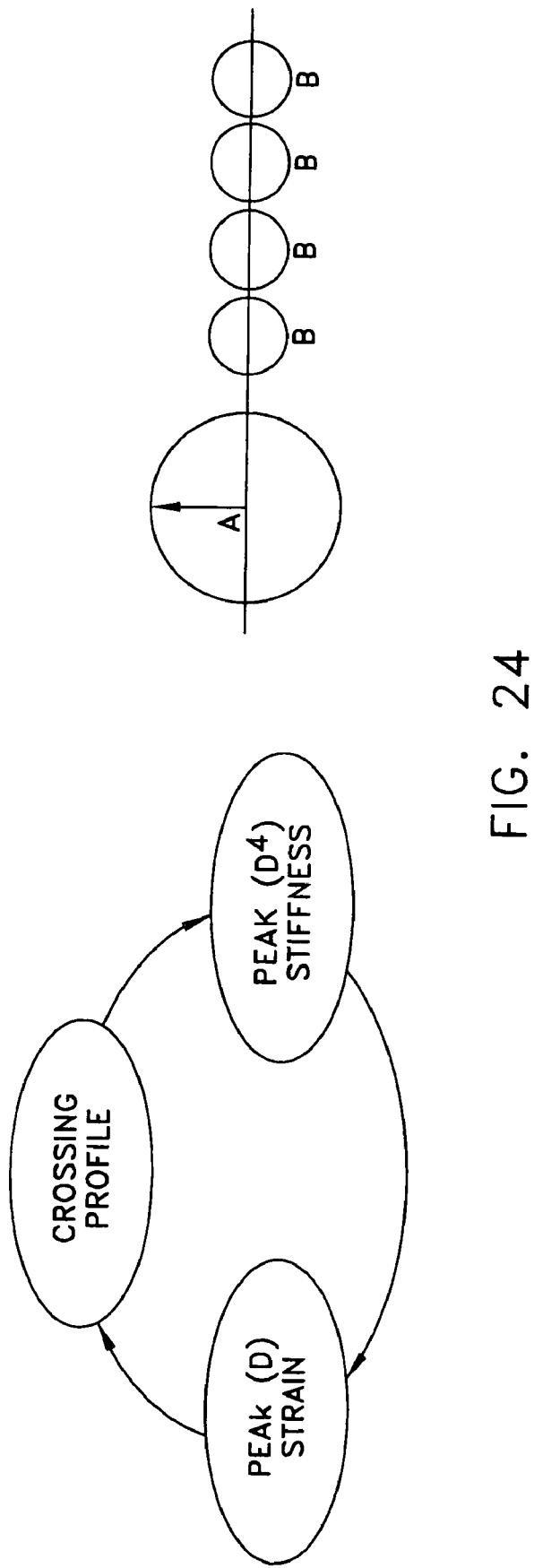
FIG. 24 is a schematic view illustrating the interrelationship between rod diameter, crossing profile, peak stiffness and peak strain.

In this respect it should also be appreciated that replacing one, relatively large diameter rod (e.g., an elongated body 157, 184 such as that discussed in the aforementioned U.S. patent application Ser. Nos. 10/446,470; 60/489,549; and 60/562,958) with a plurality of smaller rods (e.g., the straightening rods 180, 211 discussed above) yields significant advantages. More particularly, and looking now at FIG. 24, there is shown a schematic diagram illustrating the interrelationship between rod diameter (A or B), crossing profile (CP), peak stiffness (SF) and peak strain (ST). As used herein, the term "crossing profile" is meant to denote device cross-section. More particularly, as a single bar of rod diameter A is replaced by a plurality of bars having a smaller rod diameter B, the crossing profile (CP) of the implant can be reduced, the peak stiffness (SF) of the implant can be increased, and the peak strain (ST) reduced. Thus, the composite rod implant of the present invention, formed out of a plurality of small rods, can have a significant advantage over a rod implant formed out of a single, relatively large diameter rod.

It should also be appreciated that an implant device formed in accordance with the present invention presents multiple variables which can by adjusted by the doctor so as to generate different straightening forces and hence achieve optimal results. These variables include: (1) implant body position within the anatomy, (2) rod position within the implant body, (3) rod length; (4) rod stiffness; and (5) overall implant body stiffness.

It should be appreciated that inasmuch as annuloplasty device 90 can be formed with a variety of different configurations, the annuloplasty device 90 can be used for a variety of different purposes. By way of example, in one form of the invention, annuloplasty device 90 may be used solely as a diagnostic device and may be fully withdrawn at the conclusion of the procedure. In this case it may be desirable, for cost reasons, to form the annuloplasty device so that implant body 95 is formed integral (e.g., by molding) with catheter shaft 100. In another form of the invention, annuloplasty device 90 may be formed so that implant body 95 may be left at the therapy site at the conclusion of the procedure. In this situation, it may be desirable to form implant body 95 separately from catheter shaft 100, and releasably unite them together during deployment, such that implant body 95 may be left in the coronary sinus at the conclusion of the procedure.

Figure 25:
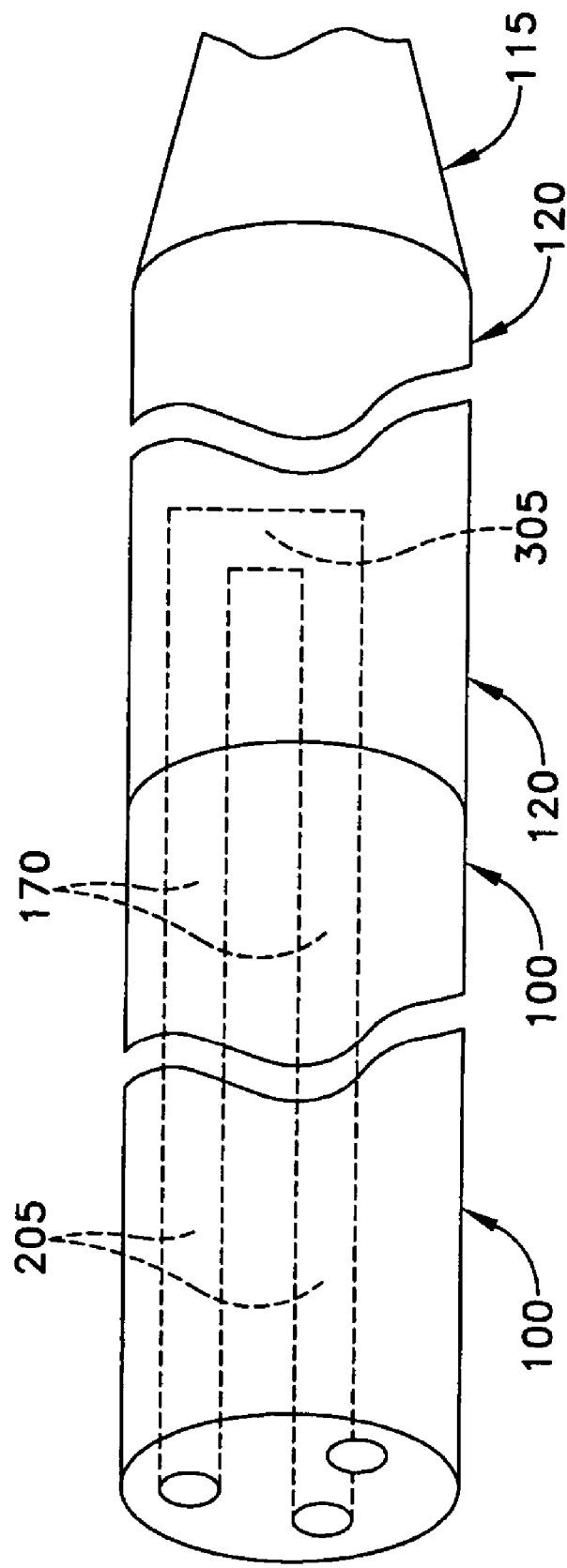
FIG. 25 is a schematic diagram illustrating how lumens may be formed so as to create a closed flow path.

In many situations it may be important to flush the device with a fluid. This may be done to eliminate air emboli, or to provide a contrast medium, or for some other purpose. In this case, and looking now at FIG. 25, in order to minimize the possibility of introducing foreign bodies to the patient, it may be desirable to connect two or more lumens at their distal ends with one or more connector portions 305, whereby to create a closed flow path. To the extent that implant body 95 is formed separable from catheter shaft 100, such that fluid must flow from working lumen 205 in catheter shaft 100 to working lumen 170 in implant body 95, it can be important to provide a fluid-tight connection between implant body 95 and catheter shaft 100.

If desired, treatment section 120 may be formed with a circular cross-section along its entire length (e.g., such as that shown in FIG. 6), or it can have a cross-section which varies along its length. By way of example but not limitation, if desired, treatment section 120 could have a circular cross-section at its distal end 150 (FIG. 26), a rectangular or trapezoidal cross-section intermediate its length (i.e., in the region adjacent to the mitral valve's P2 leaflet), and a relatively flat cross-section (FIG. 27) at its proximal end 155. Furthermore, where treatment section 120 has a cross-section other than circular, if desired, the treatment section 120 may be constrained in a circular configuration during insertion to the surgical site so as to facilitate passage of the treatment section through the vascular system of the patient. This may be achieved by enclosing treatment section 120 in a removable sheath 310 (FIG. 28) which can be removed once the treatment section 120 is disposed at the surgical site, whereby to allow treatment section 120 to assume its desired configuration.

Figure 26:
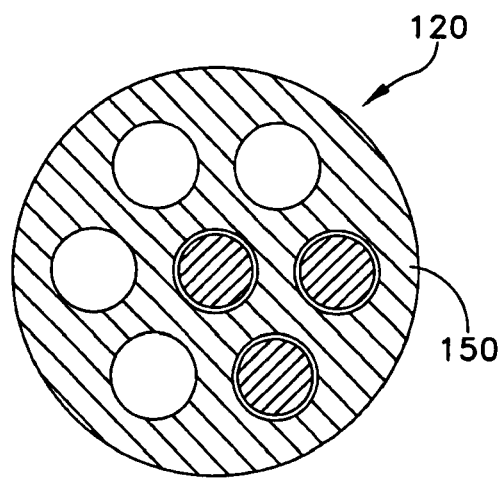
FIGS. 26–28 illustrate how the treatment section of the annuloplasty device may be formed with various cross-sections along its length.
Figure 27:
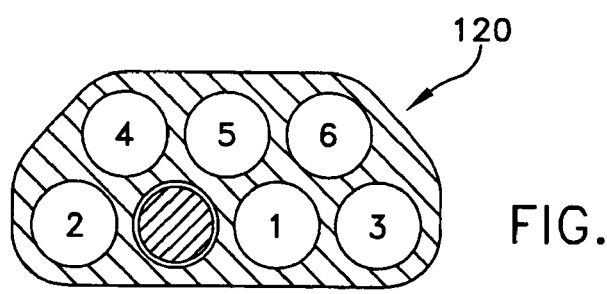
Figure 28:
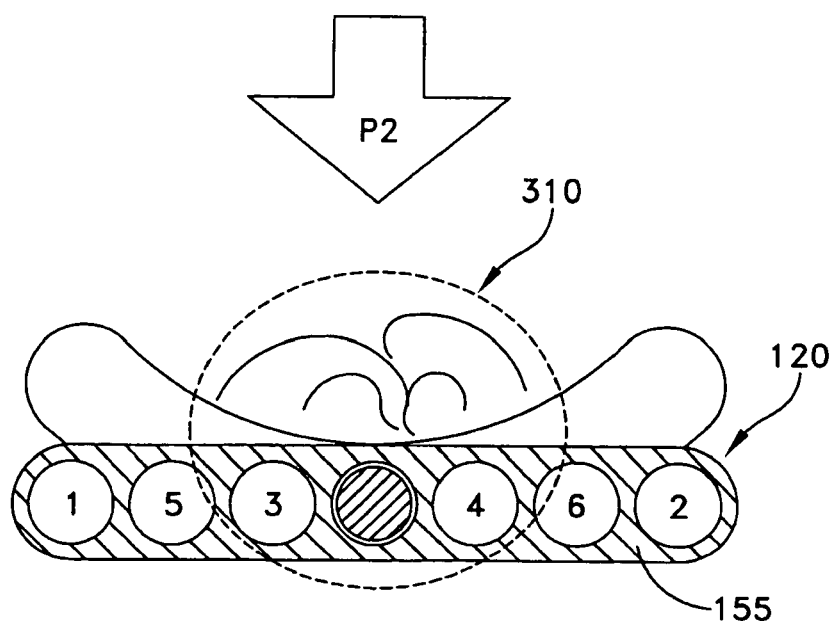
Figure 29:
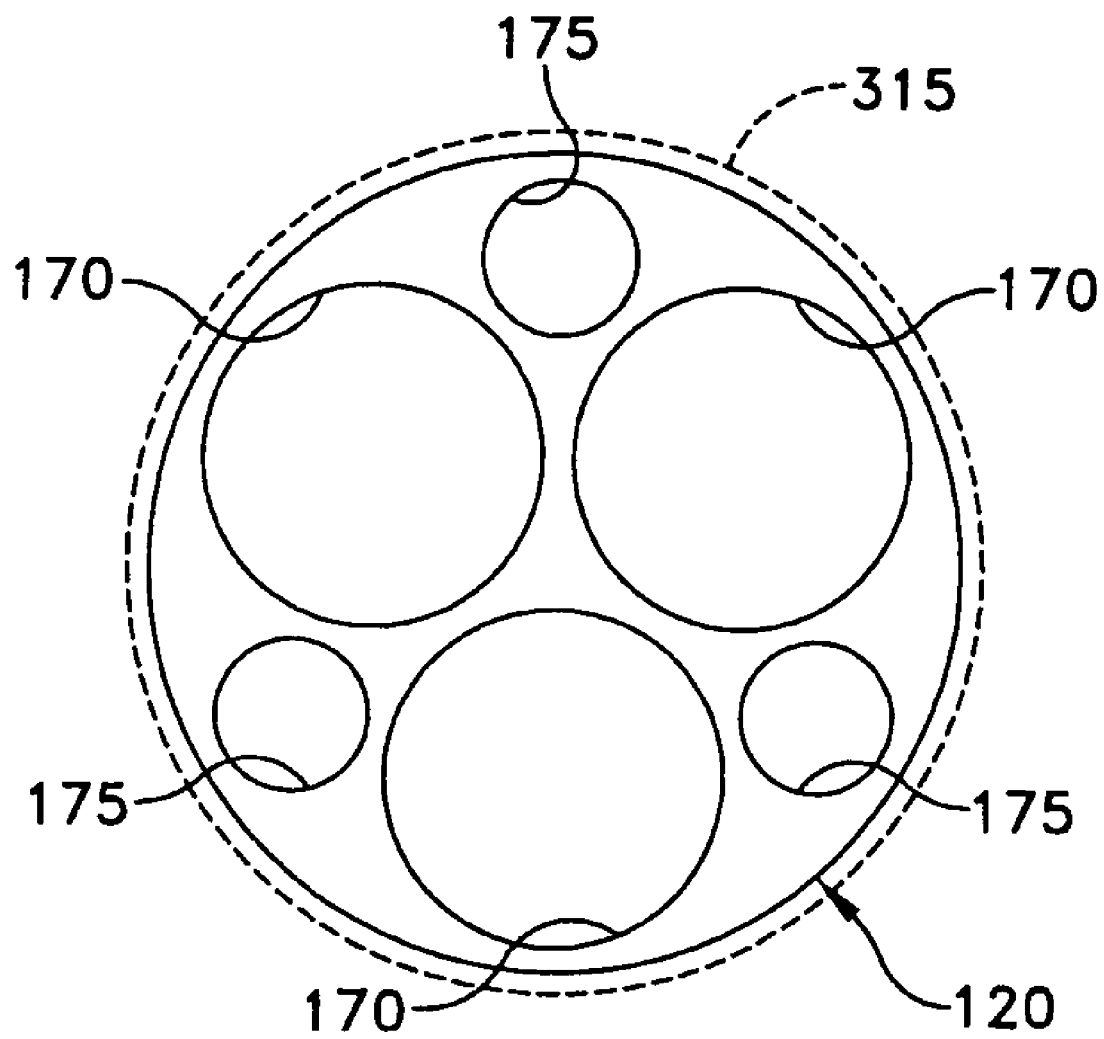
FIG. 29 illustrates how the outer surface of the annuloplasty device may be formed so as to facilitate tissue in-growth and thereby enhance device stabilization.

FIGS. 26–28 also show how the lumens extending through treatment section 120 may all have the same diameter if desired.

As noted above, implant body 95 may be deployed in conjunction with a stabilizing scaffold such as a stabilizing scaffold of the sort disclosed in the aforementioned U.S. patent application Ser. Nos. 10/446,470; 60/489,549; and 60/562,958. Such stabilizing scaffolds can help distribute device load on the wall of the coronary sinus and help stabilize the central portion of treatment section 120 against longitudinal migration (however, it will be recalled that it is generally preferred that the distal and proximal ends of the device be allowed to slide on the anatomy as needed as the device assumes a straighter configuration due to the insertion of straightening bars). Furthermore, if desired, a portion of the outer surface of treatment section 120 may comprise a construction 315 to facilitate tissue in-growth, whereby to further anchor the central portion of treatment section 120 in the coronary sinus. By way of example but not limitation, the outer surface of treatment section 120 may have an irregular, or "fuzzy" surface geometry, and/or it may be coated with tissue in-growth promoters, etc. In one preferred form of the invention, construction 315 comprises a graft element, preferably formed out of a Dacron/Teflon hybrid, anchored to the Teflon body of treatment section 120 and characterized by high traction and high endotheliazation properties.

Corridor System

Figure 30:
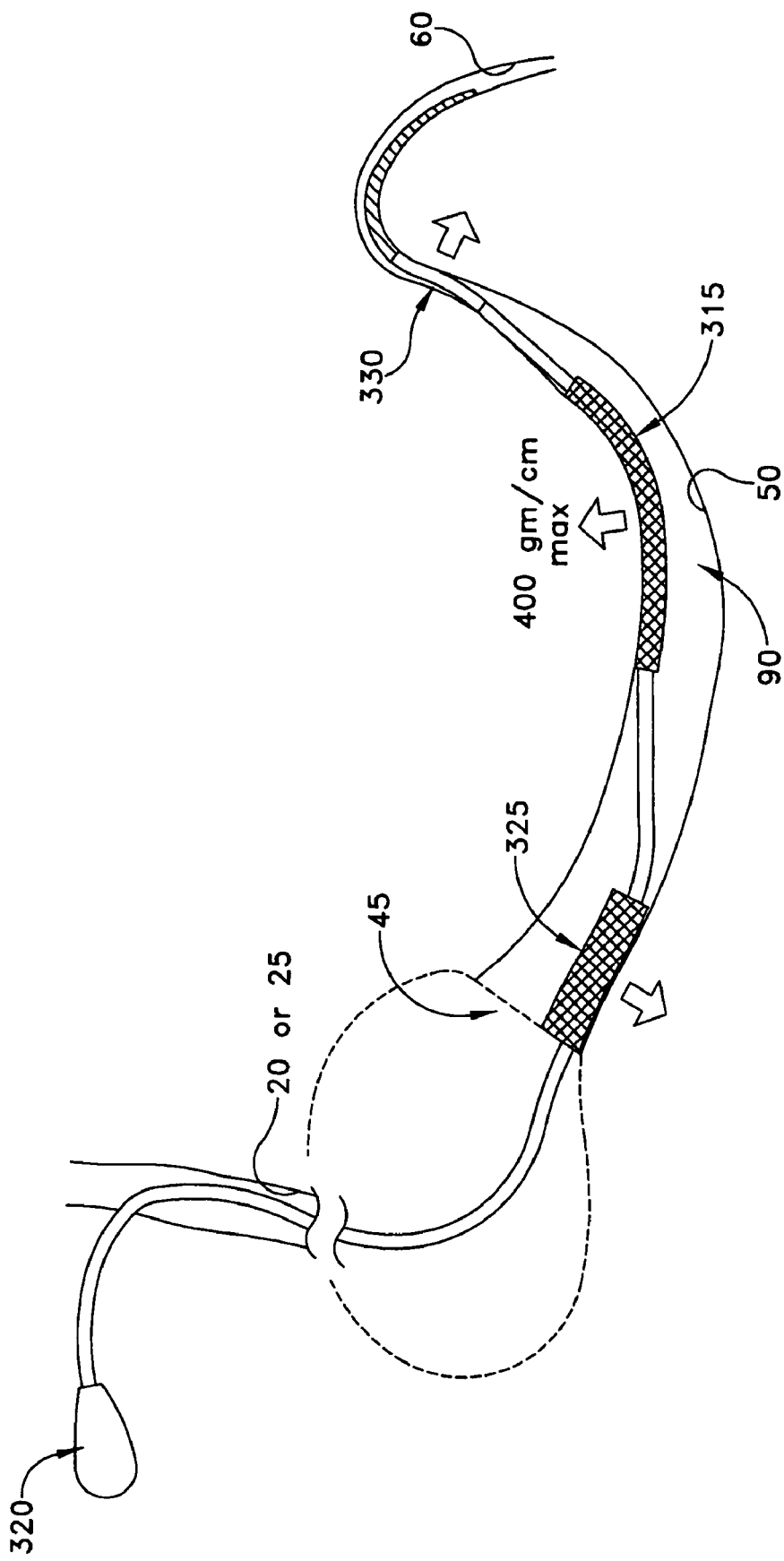
FIG. 30 is a schematic view showing another preferred form of the invention, wherein the annuloplasty device comprises a "single unit" construction and further wherein, at the conclusion of the implant procedure, the annuloplasty device has its proximal end stored in a "pocket" in the patient's chest.
Figure 31:
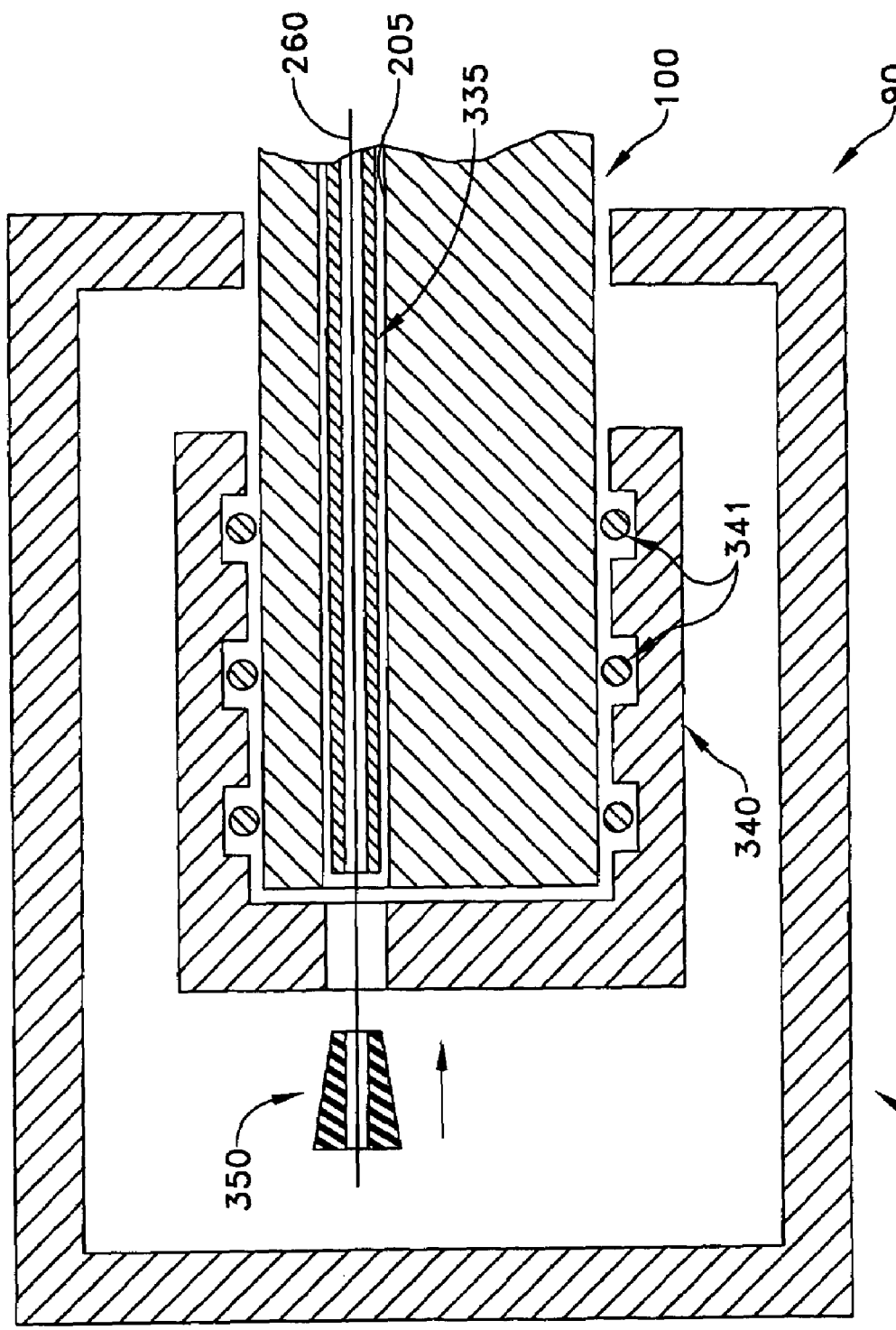
FIG. 31 is a schematic view showing how the proximal end of the annuloplasty device of FIG. 30 is capped prior to storage in the tissue pocket.

Looking next at FIGS. 30 and 31, there is shown one preferred annuloplasty device 90 which is configured to leave a re-access "corridor" extending down to implant body 95 at the conclusion of the implant procedure. To this end, (i) annuloplasty device 90 preferably comprises a "single unit" construction where the proximal end 155 of treatment section 120 and the distal end 195 of catheter shaft 100 are formed integral with one another, (ii) annuloplasty device 90 is intended to access the vascular system of the patient through a subclavian vein, and (iii) at the conclusion of the implant procedure, the proximal end of the catheter shaft is capped with a cap 320 and then secured in a "pocket" formed under the skin, as will hereinafter be discussed in further detail.

More particularly, in this form of the invention, annuloplasty device 90 is preferably deployed over a guidewire in the manner previously discussed, so that its lead section 115 extends down the AIV, treatment section 120 is deployed in the coronary sinus adjacent to the posterior leaflet of the mitral valve, and catheter shaft 100 extends through the right atrium of the heart, up the superior vena cava, up one of the subclavian veins, and then out a sidewall of that subclavian vein. In one preferred form of the invention, annuloplasty device 90 has a diameter of about 7 French.

Preferably annuloplasty device 90 extends through a support scaffold 325 which is positioned in the coronary sinus and slidingly supports the annuloplasty device near the coronary atrium 45. This support scaffold 325 may be of the sort disclosed in the aforementioned U.S. patent application Ser. Nos. 10/446,470; 60/489,549; and 60/562,958. Alternatively, this support scaffold 325 may be of any other suitable design which helps distribute the load of annuloplasty device 90 on the sidewall of the coronary sinus, and which permits the annuloplasty device 90 to slide relative to the support scaffold. Annuloplasty device 90 also preferably comprises a tissue in-growth region 315 to help anchor the central portion of treatment section 120 in the coronary sinus, and may include an anti-erosion sleeve or graft 330 about the annuloplasty device 90 at the distal end of treatment section 120.

In accordance with the foregoing description, once annuloplasty device 90 has been properly positioned within the coronary sinus, straightening rods 180 are inserted into working lumens 205, 170 so as to reconfigure the patients' anatomy and reduce mitral regurgitation.

After straightening rods 180 have been deployed in working lumens 170 so as to reconfigure the patient's anatomy and reduce mitral regurgitation, tubular bumper coils 335 (FIG. 31) or other suitable apparatus may be advanced down working lumens 205 so as to fill working lumens 205 and thereby ensure that straightening rods 180 remain stationary within working lumens 170. To the extent that straightening rods 180 also include the aforemention tension wires 260 (FIG. 18), these tension wires may extend through the interior of tubular bumper coils 335.

At this point, the proximal end of catheter shaft 100 is stored in a "pocket" in the patient's torso. More particularly, the proximal end of catheter shaft 100 is cut to size (if necessary), capped off by a cap 320, and then stored in the tissue pocket. Cap 320 may be a simple, "single unit" cap if desired or, more preferably, cap 320 may comprise an inner cap 340 (including seals 341 and plugs 350 for holding tension wires 260 in position relative to inner cap 340) and an outer cap 355 (for making a simple sliding fit over the entire back end of the annuloplasty device). Preferably outer cap 355 comprises an atraumatic profile so as to minimize any discomfort for the patient.

This "corridor system" embodiment has a number of significant advantages. Among other things, by providing an easy access corridor to the implanted device, if it should subsequently be desired to adjust the degree of tissue reconfiguration, the same can be easily accomplished, e.g., by opening the tissue pocket so as to access the distal end of annuloplasty device, removing outer cap 355, removing inner cap 340, removing tubular bumper coils 335, removing straightening rods 180 by means of tension wires 260, installing replacement straightening rods 180, reinstalling tubular bumper coils 335, and recapping the device. Alternatively, by providing an easy access corridor to the implanted device, the entire device can be subsequently removed from the patient if the same should be desired, i.e., by opening the tissue pocket so as to access the distal end of annuloplasty device, removing outer cap 355, removing inner cap 340, removing tubular bumper coils 335, removing straightening rods 180 by means of tension wires 260, and then removing the remainder of the annuloplasty device by pulling proximally on the proximal end of catheter shaft 100.

Furthermore, by providing an annuloplasty device 90 which comprises a "single unit" construction which has its proximal end sized (i.e., cut off) as needed during use so as to sit in the tissue pocket, device sizing issues (and correspondingly, inventory issues) are greatly simplified.

Modifications

It will be understood that many additional changes in the details, materials, steps and arrangements of parts, which have been herein described and illustrated in order to explain the nature of the invention, may be made by those skilled in the art within the principles and scope of the invention as expressed in the appended claims.

What is claimed is:

1. An assembly for reducing mitral regurgitation, the assembly comprising:
    an elongated carrier sufficiently flexible to assume a first configuration generally conforming to a coronary sinus upon insertion of said carrier into the coronary sinus, and to assume a straighter second configuration when biased toward the straighter configuration, said carrier having a lumen extending lengthwise therethrough; and
    an elongated rod comprising five segments disposed end-to-end, said segments comprising a central segment provided with a selected first degree of flexibility which provides rigidity sufficient to reconfigure the mitral annulus, a pair of intermediate segments, one disposed at each end of said central segment, said intermediate segments each being provided with a selected second degree of flexibility which provides more rigidity to said intermediate segments than the rigidity of said central segment, and a pair of outer segments, each disposed at the end of an intermediate segment remote from said central segment, said outer segments each being provided with a third degree of flexibility exceeding the flexibility of said central segment and said intermediate segments, said rod being adapted to be received by the lumen in said carrier;

whereby to urge said carrier from the first configuration to the second configuration, to straighten a natural curvature of at least a portion of the coronary sinus in the vicinity of the posterior leaflet of the mitral valve, to move the posterior annulus anteriorly and thereby improve leaflet coaptation and reduce mitral regurgitation.

2. An assembly according to claim 1 wherein said carrier is of a circular cross-section in at least a portion thereof.

3. An assembly according to claim 1 wherein said rod is selectable from a kit comprising a plurality of rods having different degrees of stiffness.

4. An assembly according to claim 1 wherein said rod is selectable from a kit comprising a plurality of rods having different lengths.

5. An assembly according to claim 1 wherein the assembly further comprises a guidewire, and said carrier is provided with an opening through which said guidewire is movable.

6. An assembly according to claim 1 wherein said carrier is provided with a second lumen extending lengthwise through said carrier; and said assembly comprises a second elongated rod of a material less flexible than said carrier and adapted to be received by the second lumen;

whereby to further urge said carrier from the second configuration to a still straighter configuration.

7. An assembly according to claim 6:

wherein said second rod comprises five segments disposed end-to-end, said segments comprising a central segment provided with a selected first degree of flexibility which provides rigidity sufficient to reconfigure the mitral annulus, a pair of intermediate segments, one disposed at each end of said central segment, said intermediate segments each being provided with a selected second degree of flexibility which provides more rigidity to said intermediate segments than the rigidity of said central segment, and a pair of outer segments, each disposed at the end of an intermediate segment remote from said central segment, said outer segments each being provided with a third degree of flexibility exceeding the flexibility of said central segment and said intermediate segments;

and further wherein the first rod central segment is of a stiffness different from the central segment stiffness of said second rod.

8. An assembly according to claim 6 wherein said second rod is selectable from a kit comprising a plurality of rods having different lengths.

9. An assembly according to claim 1 wherein said elongated rod is substantially straight in an unstressed condition.

10. An assembly according to claim 1 wherein said elongated rod is substantially curved after insertion into the coronary sinus.

11. An assembly according to claim 1 wherein said elongated rod central segment and said outer segments are substantially curved after said elongated rod is inserted into the coronary sinus, and said intermediate segments are substantially straight after the elongated rod is inserted into the coronary sinus.

12. An assembly according to claim 11 wherein said central segment, said outer segments and said intermediate segments have a length such that said elongated rod applies an anteriorly-directed force to the walls of the coronary sinus substantially adjacent to the posterior leaflet of the valve, and applies a posteriorly-directed force to the walls of the coronary sinus substantially adjacent to commissures of the valve.

13. An assembly according to claim 1 wherein said elongated rod is formed at least in part out of a resilient material.

14. An assembly according to claim 13 wherein said elongated rod effects valve remodeling on a continuous basis over a prolonged period of time.

15. An assembly according to claim 14 wherein said elongated rod is formed in part of a superelastic material.

16. An assembly according to claim 1 wherein said assembly further comprises a stabilizing scaffold engaging to said elongated carrier.

17. An assembly according to claim 1 wherein at least a portion of said elongated carrier is configured to facilitate tissue in-growth.

18. An assembly for reducing mitral regurgitation, the assembly comprising:

an elongated carrier of material sufficiently flexible to assume a first configuration generally conforming to a coronary sinus upon insertion of said carrier into the coronary sinus, and to assume a straighter second configuration when biased toward the straighter configuration, said carrier having a plurality of lumens extending lengthwise therethrough; and a plurality of elongated rods each comprising five segments disposed end-to-end, said segments comprising a central segment provided with a selected first degree of flexibility which provides rigidity sufficient to reconfigure the mitral annulus, a pair of intermediate segments, one disposed at each end of said central segment, said intermediate segments each being provided with a selected second degree of flexibility which provides more rigidity to said intermediate segments than the rigidity of said central segment, and a pair of outer segments, each disposed at the end of an intermediate segment remote from said central segment, said outer segments each being provided with a third degree of flexibility exceeding the flexibility of said central segment and said intermediate segments, said rods being adapted to be received by the lumens in said carrier;

whereby to urge said carrier from the first configuration to the second configuration, to straighten a natural curvature of at least a portion of the coronary sinus in the vicinity of the posterior leaflet of the mitral valve, to move the posterior annulus anteriorly and thereby improve leaflet coaptation and reduce mitral regurgitation.

19. An assembly for reducing mitral regurgitation, the assembly comprising:

a carrier sufficiently flexible to assume a first configuration generally conforming to a coronary sinus upon insertion of said carrier into the coronary sinus, and to assume a straighter second configuration when biased toward the straighter configuration, said carrier having a plurality of first lumens extending lengthwise therethrough;

a catheter shaft having a plurality of first lumens extending lengthwise therethrough, each alignable with one of the carrier first lumens, a distal end of said catheter shaft being engageable with a proximal end of said carrier;

a plurality of straightening rods, each adapted to be received by the catheter shaft first lumens and by the carrier first lumens, said rods comprising five segments disposed end-to-end, said segments comprising a central segment provided with a selected first degree of flexibility which provides rigidity sufficient to reconfigure the mitral annulus, a pair of intermediate segments, one disposed at each end of said central segment, said intermediate segments each being provided with a selected second degree of flexibility which provides more rigidity to said intermediate segments than the rigidity of said central segment, and a pair of outer segments, each disposed at the end of an intermediate segment remote from said central segment, said outer segments each being provided with a third degree of flexibility exceeding the flexibility of said central segment and said intermediate segments; and a push rod adapted to be received by at least the catheter shaft first lumens and engageable with one of said straightening rods and operable to push an engaged straightening rod into one of the carrier first lumens in alignment with one of the catheter shaft lumens in which said push rod is disposed;

whereby to bias said carrier from the first configuration to the second configuration.

20. An assembly according to claim 19 wherein said rod is selectable from a kit comprising a plurality of rods having different lengths.

21. An assembly according to claim 19 wherein the assembly further comprises a guidewire adapted for insertion into the coronary sinus, and said carrier and said catheter shaft are movable along said guidewire.

22. An assembly according to claim 19 wherein said push rod is adapted to connect to a selected straightening rod end-to-end, and to be disconnected therefrom.

23. An assembly according to claim 19 wherein said carrier and said catheter shaft are each provided with second lumens of smaller diameter than the first lumens.

24. An assembly according to claim 23 wherein tether lines are fixed in the carrier second lumens, and extend proximally from a proximal end of said catheter shaft, the tether lines being drawable through said catheter shaft to urge said catheter shaft and said carrier into abutting relationship.

25. An assembly for reducing mitral regurgitation, the assembly comprising:

an elongated carrier of material sufficiently flexible to assume a first configuration generally conforming to a coronary sinus upon insertion of said carrier into the coronary sinus, and to assume a straighter second configuration when biased toward the straighter configuration, said carrier having a plurality of first lumens extending lengthwise therethrough and a plurality of second lumens, smaller in diameter than the first lumens, extending therethrough;

a catheter shaft having a plurality of first and second lumens extending lengthwise therethrough and alignable with the respective first and second lumens of said carrier, a distal end of said catheter shaft being engageable with a proximal end of said carrier;

a plurality of straightening rods adapted to be received by the catheter shaft first lumens and by the carrier first lumens said straightening rods comprising five segments disposed end-to-end, said segments comprising a central segment provided with a selected first degree of flexibility which provides rigidity sufficient to reconfigure the mitral annulus, a pair of intermediate segments, one disposed at each end of said central segment, said intermediate segments each being provided with a selected second degree of flexibility which provides more rigidity to said intermediate segments than the rigidity of said central segment, and a pair of outer segments, each disposed at the end of an intermediate segment remote from said central segment, said outer segments each being provided with a third degree of flexibility exceeding the flexibility of said central segment and said intermediate segments;

a plurality of push rods adapted to be received by at least the catheter shaft first lumens; and a tether fixed in at least one carrier second lumen and extending through the catheter shaft second lumen and manipulatable to draw said carrier into abutting engagement with said catheter shaft;

wherein at least one selected stiffening rod is insertable into at least one selected catheter shaft first lumen, and at least one push rod is insertable into the selected catheter shaft lumen and into engagement with the selected stiffening rod to push the selected stiffening rod into one of the carrier first lumens, to bias the carrier from the first configuration towards the second configuration.

26. An assembly for reducing mitral regurgitation, the apparatus comprising:

a tubular flexible carrier adapted for insertion into a coronary sinus proximate a posterior leaflet of the mitral valve;

an elongated body comprising five segments disposed end-to-end, said segments comprising:

a central segment of sufficient rigidity to reconfigure a mitral annulus;

a pair of intermediate segments, one disposed at each end of said central segment, said intermediate segments each being of a rigidity greater that the rigidity of said central segment; and a pair of outer segments, each disposed at an end of an intermediate segment, said outer segments each being of less rigidity than the rigidity of said central segment and the rigidity of said intermediate segments;

such that upon insertion of said body into the carrier, said central segment serves to reconfigure the mitral annulus, said intermediate segments serve to transfer the load of reconfiguring the mitral annulus to said outer segments, and said outer segments serve to dissipate the load to side walls of the coronary sinus;

wherein said elongated body segments are of a length such that forces applied to walls of the coronary sinus improve leaflet coaptation by reducing a distended mitral valve anterior-to-posterior dimension without increasing the heart valve commissure-to-commissure dimension, whereby to minimize creation of commissure side jets.

27. An assembly for reducing mitral regurgitation, the assembly comprising:

an elongated carrier sufficiently flexible to assume a first configuration generally conforming to a coronary sinus upon insertion of said carrier into the coronary sinus, and to assume a straighter second configuration when biased toward the straighter configuration, said carrier having a lumen extending lengthwise therethrough; and an elongated rod having at least three different degrees of flexibility, each degree of flexibility corresponding to one or more predetermined portions of said elongated rod adapted to be received by the lumen in said carrier; whereby upon insertion of said elongated rod into said lumen of said carrier, the elongated rod urges said carrier from the first configuration to the second configuration resulting in a straightening of a natural curvature of at least a portion of the coronary sinus in the vicinity of the posterior leaflet of the mitral valve when the carrier is inserted into the coronary sinus, wherein said elongated rod comprises a central segment provided with a selected first degree of flexibility which provides rigidity sufficient to reconfigure the mitral annulus, a pair of intermediate segments, one disposed at each end of said central segment, said intermediate segments each being provided with a selected second degree of flexibility which provides more rigidity to said intermediate segments than the rigidity of said central segment, and a pair of outer segments, each disposed at the end of an intermediate segment remote from said central segment, said outer segments each being provided with a third degree of flexibility exceeding the flexibility of said central segment and said intermediate segments.

28. An assembly according to claim 27 wherein said elongated rod central segment and said outer segments are substantially curved after said elongated rod is inserted into the coronary sinus, and intermediate segments are substantially straight after the elongated rod is inserted into the coronary sinus.

29. An assembly according to claim 28 wherein said central segment, said outer segments and said intermediate segments have a length such that said elongated rod applies an anteriorly-directed force to the walls of the coronary sinus substantially adjacent to the posterior leaflet of the valve, and applies a posteriorly-directed force to the walls of the coronary sinus substantially adjacent to commissures of the valve.

* * * * *